(12) United States Patent
Molenberg et al.

(10) Patent No.: US 8,282,912 B2
(45) Date of Patent: *Oct. 9, 2012

(54) COMPOSITIONS FOR TISSUE AUGMENTATION

(75) Inventors: Aaldert Rens Molenberg, Binningen (CH); Enrico Zamparo, Zurich (CH); Laurent Rapillard, Fully (CH); Simona Cerritelli, Zurich (CH)

(73) Assignee: Kuros Biosurgery, AG, Zurich (CH)

( * ) Notice: Subject to any disclaimer, the term of this patent is extended or adjusted under 35 U.S.C. 154(b) by 260 days.

This patent is subject to a terminal disclaimer.

(21) Appl. No.: 12/500,843

(22) Filed: Jul. 10, 2009

(65) Prior Publication Data

US 2010/0034769 A1 Feb. 11, 2010

Related U.S. Application Data

(63) Continuation-in-part of application No. 10/395,650, filed on Mar. 21, 2003, now Pat. No. 7,575,740.

(60) Provisional application No. 60/366,712, filed on Mar. 22, 2002, provisional application No. 60/408,077, filed on Sep. 4, 2002.

(51) Int. Cl.
*A61K 31/74* (2006.01)
*A61F 13/00* (2006.01)
*A61F 2/00* (2006.01)

(52) U.S. Cl. ............... 424/78.08; 424/423; 424/422

(58) Field of Classification Search .................. 424/423, 424/78.08, 422

See application file for complete search history.

(56) References Cited

U.S. PATENT DOCUMENTS

| | | | |
|---|---|---|---|
| 3,908,039 | A | 9/1975 | Guthrie et al. |
| 4,711,903 | A | 12/1987 | Mueller et al. |
| 4,835,297 | A | 5/1989 | Deschler et al. |
| 5,268,305 | A | 12/1993 | Ribi et al. |
| 5,292,514 | A | 3/1994 | Cappechi et al. |
| 5,294,690 | A | 3/1994 | Iguchi et al. |
| 5,330,911 | A | 7/1994 | Hubbell et al. |
| 5,410,016 | A | 4/1995 | Hubbell et al. |
| 5,427,915 | A | 6/1995 | Ribi et al. |
| 5,428,014 | A | 6/1995 | Labroo et al. |

(Continued)

FOREIGN PATENT DOCUMENTS

CA 2281602 8/1999

(Continued)

OTHER PUBLICATIONS

Pacios et al., J. Phys. Chem. A 2000, 104, 7617-7624.*

(Continued)

*Primary Examiner* — Blessing Fubara
(74) *Attorney, Agent, or Firm* — Pabst Patent Group LLP

(57) ABSTRACT

Methods for making biomaterials for augmentation of soft and hard tissues, kits containing precursors for forming the biomaterials, and the resulting biomaterials are described herein. The biomaterials are formed from at least a first and a second precursor component. The first precursor component contains at least two nucleophilic groups, and the second precursor component contains at least two electrophilic groups. The nucleophilic and electrophilic groups of the first and second precursor components form covalent linkages with each other at physiological temperatures. The precursors are selected based on the desired properties of the biomaterial. In the preferred embodiment, the first precursor is a siloxane. Optionally, the biomaterials contain additives, such as thixotropic agents, radiopaque agents, or bioactive agents. In the preferred embodiment, the biomaterials are used to augment at least one vertebra of the spine (vertebroplasty).

30 Claims, 4 Drawing Sheets

U.S. PATENT DOCUMENTS

| | | | |
|---|---|---|---|
| 5,446,090 A | 8/1995 | Harris | |
| 5,527,856 A | 6/1996 | Rhee et al. | |
| 5,529,914 A | 6/1996 | Hubbell et al. | |
| 5,567,422 A | 10/1996 | Greenwald | |
| 5,573,934 A | 11/1996 | Hubbell et al. | |
| 5,612,390 A | 3/1997 | Iguchi et al. | |
| 5,626,863 A | 5/1997 | Hubbell et al. | |
| 5,635,207 A | 6/1997 | Grinstaff et al. | |
| 5,752,974 A | 5/1998 | Rhee et al. | |
| 5,874,500 A * | 2/1999 | Rhee et al. | 525/54.1 |
| 5,876,805 A | 3/1999 | Ostlie | |
| 5,897,955 A | 4/1999 | Drumheller | |
| 5,932,462 A | 8/1999 | Harris et al. | |
| 5,958,874 A | 9/1999 | Clark et al. | |
| 6,051,648 A | 4/2000 | Rhee et al. | |
| 6,136,564 A | 10/2000 | Kopetzki | |
| 6,165,486 A * | 12/2000 | Marra et al. | 424/423 |
| 6,166,130 A | 12/2000 | Rhee et al. | |
| 6,258,351 B1 | 7/2001 | Harris | |
| 6,277,502 B1 | 8/2001 | Buchecker et al. | |
| 6,312,725 B1 | 11/2001 | Wallace et al. | |
| 6,384,107 B2 * | 5/2002 | Liu | 523/118 |
| 6,458,889 B1 | 10/2002 | Trollsas et al. | |
| 6,534,591 B2 | 3/2003 | Rhee et al. | |
| 6,566,406 B1 | 5/2003 | Pathak et al. | |
| 6,624,245 B2 | 9/2003 | Wallace et al. | |
| 6,639,046 B1 | 10/2003 | Van Dijk | |
| 6,653,420 B2 * | 11/2003 | Domschke et al. | 526/258 |
| 6,833,408 B2 | 12/2004 | Sehl et al. | |
| 6,958,212 B1 | 10/2005 | Hubbell et al. | |
| 7,009,034 B2 | 3/2006 | Pathak et al. | |
| 7,176,256 B2 | 2/2007 | Rhee et al. | |
| 7,247,609 B2 | 7/2007 | Lutolf | |
| 7,273,896 B2 | 9/2007 | Daniloff et al. | |
| 7,291,673 B2 | 11/2007 | Hubbell | |
| 7,332,566 B2 | 2/2008 | Pathak et al. | |
| 7,413,739 B2 | 8/2008 | Hubbell | |
| 7,575,740 B2 * | 8/2009 | Molenberg et al. | 424/78.08 |
| 7,592,418 B2 | 9/2009 | Pathak et al. | |
| 7,670,605 B2 | 3/2010 | Hubbell | |
| 7,744,912 B1 | 6/2010 | Hubbell | |
| 2003/0044468 A1 | 3/2003 | Cellesi et al. | |
| 2003/0059906 A1 | 3/2003 | Hubbell et al. | |
| 2004/0234708 A1 | 11/2004 | Matsuki et al. | |
| 2005/0027070 A1 | 2/2005 | Rhee et al. | |
| 2005/0245721 A1 | 11/2005 | Beckley et al. | |
| 2007/0032568 A1 | 2/2007 | Lin et al. | |

FOREIGN PATENT DOCUMENTS

| | | |
|---|---|---|
| EP | 1 462 501 | 9/2004 |
| EP | 1 593 727 | 11/2005 |
| GB | 1348045 | 3/1974 |
| JP | 2000-502380 | 10/2008 |
| WO | WO 97/22371 | 6/1997 |
| WO | WO 00/09087 | 2/2000 |
| WO | WO 00/33764 | 6/2000 |
| WO | WO 00/44808 * | 8/2000 |
| WO | WO 00/64959 | 11/2000 |
| WO | 0116210 | 3/2001 |
| WO | WO 01/54746 | 8/2001 |
| WO | WO 03/040235 | 5/2003 |
| WO | WO 03/080144 | 10/2003 |

OTHER PUBLICATIONS

Deramond, et al., "Percutaneous vertebroplasty with polymethylmethacrylate. Technique, indications, and results.", 36(3):533-546 (1998).

Ferguson, et al., "Evaluation of adjacent segment failure following vertebroplasty", *Trans. 47th Ann. Meet. ORS*, abstract 02080 (2001).

Hern, et al., "Incorporation of adhesion peptides into nonadhesive hydrogels useful for tissue resurfacing.", *J. Biomed Mater. Res.*, 39:266-276 (1988).

Luginbuehl, et al., "Localized Delivery of Growth Factors for Bone Repair", *Eur. J. Pharm. Biopharm.*, 58:197-208 (2004).

Mathis, et al., "Percutaneous vertebroplasty: a developing standard of care for vertebral compression fractures", *Am. J. Neuroradiol.*, 22:373-381 (2001).

Michel, et al., "Compressive fatigue behavior of bovine trabecular bone," *J. Biomechanics* 26:453-463 (1993).

Cellesi, et al., "Towards a fully-synthetic substitute of alginate: development of a new process using thermal gelation and chemical cross-linking", Biomaterials, 25:5115-24 (2004).

* cited by examiner

COMPOSITIONS FOR TISSUE AUGMENTATION

CROSS-REFERENCE TO RELATED APPLICATIONS

This application is a continuation-in-part of U.S. Ser. No. 10/395,650, filed Mar. 21, 2003, now U.S. Pat. No. 7,57,740 entitled "Compositions for Tissue Augmentation" to Aaldert Rens Molenberg, Daniel Fehr, and Nicola Tirelli, which claims priority to U.S. Application No. 60/366,712, filed Mar. 22, 2002, entitled "Compositions for Tissue Augmentation" to Aaldert Rens Molenberg, Daniel Fehr, and Nicola Tirelli and to U.S. Application No. 60/408,077, filed Sep. 4, 2002, entitled "Compositions for Tissue Augmentation" to Aaldert Rens Molenberg, Daniel Fehr, and Nicola Tirelli.

FIELD OF THE INVENTION

The present invention relates to biomaterials for tissue augmentation, precursor components capable of forming the biomaterials and, methods of making and using thereof. In particular, the present invention relates to the in situ formation of biomaterials for augmentation of soft and/or hard tissues.

BACKGROUND OF THE INVENTION

Synthetic materials have been investigated for implantation in the body to assist in surgical reconstruction and repair. Biomaterials of synthetic polymeric origin have been used for tissue related applications, such as tissue regeneration matrices, tissue adhesives, drug delivery matrices, for the prevention of surgical adhesions, as coatings for synthetic implants and as tissue augmentation materials. Depending on the chemical structure of the precursor components and their stoichiometry, the biomaterials have varying physical and chemical properties.

Orthopedic Surgery

Orthopedic surgery has historically been the most significant application for biomaterials. Orthopedics deals the musculoskeletal system and the treatment of diseases and disturbances to its components, particularly bones, cartilage, ligaments, and tendons. The musculoskeletal system produces movement and responds to forces; therefore it is susceptible to injury and stress-related diseases, which can adversely affect mobility. Further, as part of the aging process, tissue changes its shape and consistency. In particular, some tissues lose their form; thus augmentation or restoration is desirable. The loss of bone mass and stability, as occurs in osteoporosis, can be particularly devastating to an individual. A number of other diseases also adversely affect bone and joint function, leading to pain, loss of movement, and/or loss of vital function. One such prominent example is osteoarthritis, which is largely a mechanical disruption to the cartilage and underlying bone at the joints.

Any material used as a replacement and/or for enforcement of these tissues has to have mechanical properties equivalent to the tissue it is replacing and/or enforcing.

Hard Tissue Augmentation

Although a biomaterial used for augmenting hard tissue can be applied in different ways, a particular preferred way is through minimal invasive surgery. Compression fractures are particularly problematic in osteoporotic women. Minimally invasive surgery is the procedure of choice for treating vertebral compression fractures or osteoporotic vertebrae. This treatment is known as vertebroplasty. Before vertebroplasty was developed, surgeons did not treat compression fractures because intervention in these patients was risky and adequate tools were not available. In response, vertebroplasty, a procedure in which the vertebral body is filled percutaneously with polymethylmethacrylate (PMMA), was developed.

PMMA is mainly used as bone cement and is used off-label in this indication. PMMA is a hard, brittle polymer, tolerated by tissues and generally resistant to degradation. PMMA as used in vertebroplasty is a powder liquid system (PMMA co-polymer/monomeric methylmethacrylate) mixed in the operation room to form a viscous paste and pulled up into a syringe immediately prior to injection into the vertebra.

Vertebroplasty can be effective for treating compression fractures. It relieves pain in the majority of cases by preventing the micro-movement of the spongy tissue structure inside the vertebra and providing mechanical stabilization of existing microfractures (Mathis J. et al., *Am. J. Neuroradiol.* 22: 373-381 (2001)). The risk factors and problems in vertebroplasty are mainly associated with the material itself The highly toxic methylmethacrylate may leach out into the blood stream before it is crosslinked sufficiently, causing blood pressure drop and migration of the bone cement into the veins, or cause hypotension. Migration of MMA through the blood stream can result in the accumulation of this material in organs, such as the lungs. Although this is a risk common to all uses of PMMA, it is increased in vertebroplasty due to the fact that PMMA is injected under pressure into a closed space inside fractured bone. This increases the risk for leakage. The exothermic polymerization process is a further deficiency of PMMA since it often leads to substantial damage of the surrounding tissue due to the generation of significant amounts of heat. Thus, PMMA is far from the ideal biomaterial for hard tissue augmentation, in general, and for vertebroplasty, in particular.

Handling is also an issue. The final preparation of the PMMA mixture has to be performed in the operation room. The individual components are measured, mixed to form a homogenous mixture, and the mixture is filled into the appropriate device for application, which is typically a syringe for vertebroplasty. This procedure is time-consuming, susceptible to mistakes, and creates potential health hazards for the person preparing the PMMA due to inhalation of the powder and volatile methylmethacrylate during mixing.

Even after successful injection and polymerization, PMMA can cause complications. PMMA is very hard and can cause stress-shielding and/or collapse of the vertebrae adjacent to the treated vertebra which then may fracture as well. (Ferguson S. et al, *Transactions of the 47th Annual Meeting of the ORS*, 0280 (2001)).

Compositions which have to form biomaterials at the site of injection in the human or animal body and which have to augment osteoporotic vertebrae have to meet various criteria. First, the treatment should reduce or completely remove the pain associated with fractured vertebrae so that the patient can leave the bed and increase mobility. Second, the mechanical properties of the osteoporotic vertebra must be improved. This is evident when comparing compressive strength and Young's modulus E of a young healthy vertebra (vertebra in its ideal state) to an osteoporotic vertebra. The compressive strength of the spongy inner part of an ideal vertebra can be up to eightfold greater than that of an osteoporotic vertebra. Similarly, the Young's modulus E of the spongy part of an ideal vertebra can be up to a hundredfold greater than the Young's modulus E of an osteoporotic one. It is accepted that the mechanical properties of an ideal vertebra can hardly be re-established but people suffering from osteoporosis are mainly at an advanced age and do not seek to undertake great physical efforts which require the presence of ideal vertebrae.

Thus as long as the patient is free of pain and has regained mobility to a substantial part of his vertebrae, the treatment is deemed successful.

Biomaterials which are made from polymeric hydrophilic systems, such as PEG derivatives, have been described in the prior art, such as in U.S. Pat. Nos. 5,626,863; 6,166,130; 6,051,648; 5,874,500; 6,258,351 and in WO 00/44808. These biomaterials are not suitable for use in hard tissue augmentation due to insufficient strength and stiffness and their tendency to swell extensively when exposed to aqueous media, such as physiological fluids. Uncontrollable swelling makes biomaterials unacceptable for application in limited spaces as in vertebrae. As the material expands, it can press against nerves, such as the spinal cord, or protrude uncontrollably from the place of injection.

Therefore, there exists a need for improved biomaterials which can be used for hard tissue augmentation. In particular due to the growth in the elderly population, there is a need for a replacement material for PMMA for use in vertebroplasty.

It is therefore an object of the present invention to provide a biomaterial for tissue augmentation.

It is a further object of the present invention to provide a biomaterial for hard tissue augmentation, preferably as a replacement for PMMA.

It is a further object to provide an augmentation material for use in vertebroplasty which does not have the disadvantages and risks associated with the use of PMMA.

SUMMARY OF THE INVENTION

Biomaterials for augmentation of soft and hard tissues, precursors for forming the biomaterials, and methods of making and using thereof are described herein. The biomaterials are formed from at least a first and a second precursor component. The first precursor component contains at least two nucleophilic groups, and the second precursor component contains at least two electrophilic groups. In a preferred embodiment, the sum of the number of nucleophilic groups and electrophilic groups is greater than or equal to 5.

The nucleophilic and electrophilic groups of the first and second precursor components form covalent linkages with each other at physiological conditions (e.g., temperature, pH, etc.). The precursors are selected based on the desired properties of the biomaterial. The precursor molecules can be monomers, oligomers, and/or polymers. In a preferred embodiment, the precursor molecules are monomers and/or oligomers. In a particularly preferred embodiment, the precursor components are monomers. In one embodiment, the biomaterial is formed by the reaction of a first precursor component containing at least tetra(3-mercaptopropyl)silane and a second precursor component containing at least dipentaerythritol penta-acrylate. The biomaterials can further contain additives, such as thixotropic agents, contrast agents (e.g., $BaSO_4$), radiopaque agents, bioactive agents, and combinations thereof.

In one embodiment, the biomaterial is formed in situ by applying a composition containing at least a first and a second precursor component, wherein the first precursor component contains at least m nucleophilic groups and the second precursor component contains at least n electrophilic groups, wherein m+n is at least five, and wherein the first and second precursor components crosslink under physiological conditions over a period of time following application to form a polymeric network in a biomaterial. The precursor components can be formulated as solutions (i.e., dissolved in a solvent or co-solvent). In another embodiment, the precursor components are liquids at room temperature and can be used neat (i.e., in the absence of a solvent or co-solvent). The materials are characterized by the fact that they do not swell extensively when exposed to aqueous media, such as physiological, unlike prior art biomaterials prepared from synthetic polymers, such as PEG. In one embodiment, the uptake of water by the biomaterial formed by reaction of the first and second precursor components does not exceed 7% by weight of the weight of the biomaterial before it is stored for one year at 37° C. in water or in a buffer solution.

The biomaterial can be utilized in a wide variety of orthopedic, periodontal, and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, intermaxillary fixation of fractures, mentoplasty, temporomandibular joint replacement, inlay osteoimplants, implant placement and revision, and combinations thereof. However, the precursor components can also be tailored to produce biomaterials that are suitable for other types of tissue augmentation. In one embodiment, the biomaterials can be used to augment hard tissue, such as vertebrae of the spine (e.g., vertebroplasty).

DETAILED DESCRIPTION OF THE INVENTION

I. Definitions

Figure 1A:
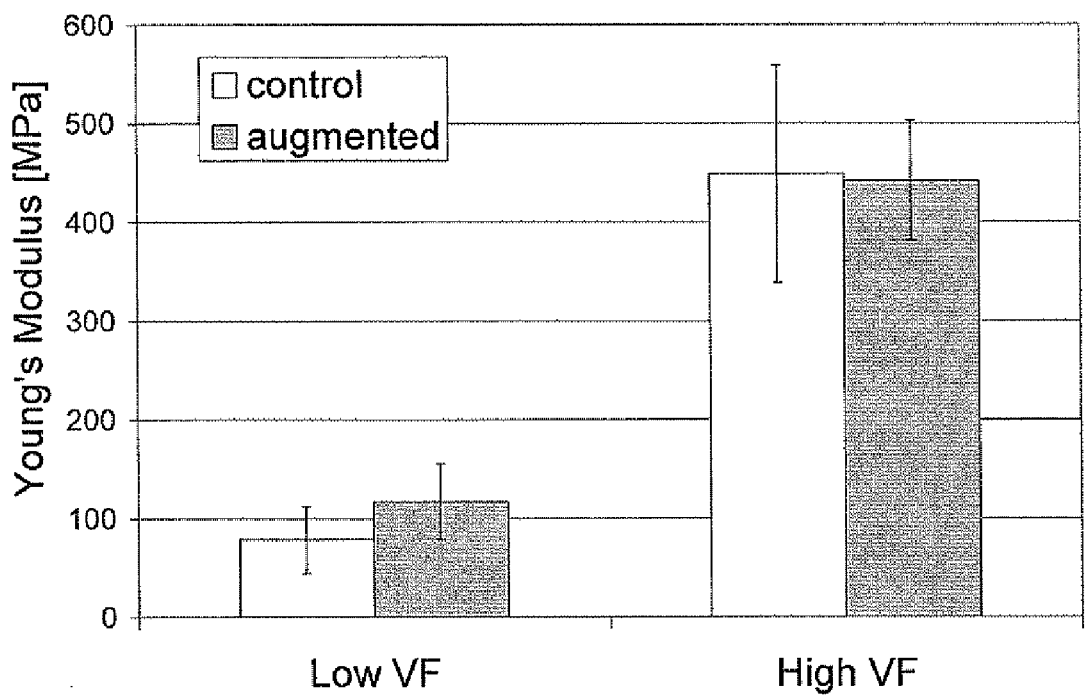
FIG. 1A shows a comparison of Young's modulus (MPa) between a control and an augmented group of vertebrae for both low and high volume fractions (VF) (*p<0.05).

"Biomaterial" or "Pharmaceutical composition" as generally used herein refers to a material intended to interface with biological systems to evaluate, treat, augment, or replace any tissue, organ or function of the body. Biomaterial refers to the complete material (precursor plus all additives, bioactive agents, fillers, initiators (e.g., base) and/or solvents, etc.) at and after having reached and passed its gel-point.

"Mixture of precursor components" as generally used herein refers to the precursor components after being mixed and before the mixture has reached its gel-point.

"Nucleophilic group" or "nucleophile" as used herein generally refers to functional groups that can donate an electron pair to form a covalent bond. Examples include, but are not limited to, thiols, amines, alkoxides, phenoxides, and combinations thereof.

"Conjugation" can refer both to alternation of carbon-carbon, carbon-heteroatom or heteroatom-heteroatom multiple bonds with single bonds, or to the linking of a functional group to a macromolecule, such as a synthetic polymer or a protein. Double bonds spaced by a CH or $CH_2$ unit are referred to as "homoconjugated double bonds".

"Biocompatibility" or "biocompatible" as generally used herein refers to the ability of a material to perform with an appropriate host response in a specific application. In the broadest sense, this means a lack of adverse effects to the body in a way that would outweigh the benefit of the material and/or treatment to the patient.

"In situ formation" as generally used herein refers to the ability of mixtures of precursor components which are substantially not crosslinked prior to injection to form covalent linkages with each other under physiological conditions (e.g., temperature, pH, etc.) during injection and at the site of injection in the body of the animal host.

"Oligomer" and "polymer" are used in the conventional sense. An oligomer is a low-molecular weight polymer. Oligomers typically contain between two and ten monomer units. As used herein, polymers typically contain more than 10 monomeric units.

"Cross-linking" as generally used herein means the formation of covalent linkages.

"Functionality" as generally used herein means the number of reactive sites on a molecule. "Reactive sites" refer to nucleophilic and electrophilic groups that are able to react in a self-selective reaction at least but not exclusively under conditions in the human or animal body.

"Multifunctional" as generally used herein means more than one electrophilic and/or nucleophilic functional group per molecule (i.e. monomer, oligomer or polymer).

"Self selective reaction" as generally used herein means that the first precursor component of the composition reacts much faster with the second precursor component of the composition and vice versa than with other compounds present in the mixture and/or at the site of the reaction. As used herein, the nucleophile preferentially reacts with an electrophile, rather than to other biological compounds, and an electrophile preferentially reacts with a nucleophile rather than with other biological compounds.

"Polymeric network" means the product of a process in which substantially all of the monomers, oligomers, or polymers are bound by intermolecular covalent linkages through their available functional groups to form a macromolecule.

"Physiological conditions" means conditions as they can be found in living vertebrates. In particular, physiological conditions refer to the conditions in the human body such as temperature, pH, etc. "Physiological temperature" means in particular a temperature range of between 35° C. to 42° C., preferably around 37° C.

"Soft tissue" means non-skeletal tissue, i.e. exclusive of bones, ligaments, cartilage, spinal disc and fibrous tissue.

"Hard tissue" means bone and/or cartilage. In one embodiment, hard tissue refers to bone.

"Augmentation" means the act of augmenting, making larger and particularly making stronger by addition and increase of material; furthermore it means the state of being augmented; as used herein augmentation means in particular to strengthen tissue; augmentation also encompasses cementation of artificial joints like artificial hips and knees within the body.

"Crosslink density" is defined as the average molecular weight between two crosslinks ($M_c$) of the respective molecules.

"Hydrogel" means a class of polymeric material which swell extensively in an aqueous medium, but which do not dissolve in water.

"Swelling" means the increase in volume and/or mass due to the uptake of water by the biomaterial. The terms "water-uptake" and "swelling" are used synonymously throughout the application.

"Compressive strength" means the maximum stress a material can sustain under crush loading. Compressive strength is calculated by dividing the maximum load by the original cross-sectional area of a specimen in a compression test.

"Thixotropic fluids" refer to fluids which show a time dependent response to shear. When subjected to a fixed shear rate, they will decrease in viscosity over time. Often this is seen as a large initial viscosity loss, followed by gradual further loss. Once shear is removed, thixotropic fluids recover viscosity. These fluids are usually considered pseudoplastic as well, but only in that they show decreasing viscosity in response to increasing shear rate. Pseudoplastic fluids are commonly considered simply shear-thinning. More specifically, they show decreasing viscosity in response to increasing shear rate. Moreover, they immediately recover their non-sheared viscosity once shear is removed.

"Stiffness" is defined as measure of resistance of plastic to bending. It includes both plastic and elastic behavior. Stiffness of the biomaterials is measured by measurement of Young's modulus E.

"Strain" is change per unit length in a linear dimension of a part or specimen, usually expressed in % strain based on original length of the specimen ($\Delta L/L_o$). True or natural strain is based on instantaneous length, and is equal to ln×lo, where l is instantaneous length and lo is original length of the specimen. Shear strain is the change in angle between two lines originally at right angles.

"Stress" is defined as load on specimen divided by the area through which it acts and generally contains units of Pa or MPa. As used with most mechanical tests, stress is based on original cross-sectional area without taking into account changes in area due to applied load. This sometimes is called conventional or engineering stress. True stress is equal to the load divided by the instantaneous cross-sectional area through which it acts.

"Modulus of Elasticity/Young's modulus E" is defined as the rate of change of strain as a function of stress and generally contains units of Pa or MPa. Young's Modulus is the slope of the straight line portion of a stress-strain diagram. Tangent modulus of elasticity is the slope of the stress-strain diagram at any point. Depending on the type of loading represented by the stress-strain diagram. Modulus used alone generally refers to tensile modulus of elasticity (or modulus of elasticity in tension). Moduli of elasticity in tension and modulus of elasticity in compressive are approximately equal and are known as Young's modulus.

"Gel point" is defined as being the point where the viscous modulus and complex modulus cross each other and viscosity increases. The viscous modulus is at the end lower that at the beginning, the complex modulus is at the end higher than at the beginning. Thus the gel point is the stage at which a liquid begins to take on the semisolid characteristics of a gel.

II. Compositions

A composition, which is crosslinked in situ, for the manufacture of a pharmaceutical composition or biomaterial for augmenting soft and/or hard tissue is described herein. In one embodiment, the biomaterial is used to augment hard tissue, such as bone. The composition contains at least a first and a second multifunctional precursor component. Optionally additives and/or biologically active agents may be added to the precursor components. The precursor components are mixed and crosslinked or polymerized in situ to form a biomaterial. The particular precursor components are selected based on the desired properties of the biomaterial.

A. Precursors

The first precursor component contains at least two nucleophilic groups, and the second precursor component contains at least two electrophilic groups. In one embodiment, the functionality of the first and/or second precursor component is at least three and the sum of the number of nucleophilic and electrophilic groups is at least 5. In a preferred embodiment, the first precursor component has a functionality of four, and the second precursor component a functionality of five. The first and second precursor components are selected such that the nucleophilic and electrophilic groups form covalent linkages under physiological conditions.

The precursor components are multifunctional monomers, oligomers and/or polymers. In one embodiment, the precursor components are multifunctional monomers and oligomers. In another embodiment, the precursor components are multifunctional monomers. Preferably the molecular weight of the first and/or second precursor component is in a range of between 100 g/mol to 900 g/mol, preferably 200 g/mol to 700 g/mol and even more preferably 400 g/mol to 550 g/mol.

The precursor components can be dissolved in a solvent or co-solvent prior to mixing the precursor components. However, in a preferred embodiment, the first and the second precursor components are liquids at room temperature, and are used neat (i.e., without first solubilizing the precursor components in a solvent or cosolvent).

While the functionality of the precursor components is a factor to consider in designing a biomaterial, it is not the prerequisite for the polymeric network to form a biomaterial with the mechanical properties needed for hard tissue augmentation, such as vertebroplasty, because the mechanical performance of the biomaterial also depends on the structure of the molecule as a whole. A small and compact molecule will form a polymeric network with greater strength than an extended molecule, although the functionality, molecular weight and reaction partner might be the same for both molecules. For example, a biomaterial formed by crosslinking monomer to monomer or monomer to oligomer is more compact than a biomaterial formed by crosslinking polymeric precursor components.

As a general guideline, the ratio of the first and second precursor components is selected such that the majority of the functional groups of both components react with their respective counterparts. The ratio of the number of the electrophilic groups (second precursor component) and the nucleophilic groups (first precursor component) is in the range of between 0.7 and 1.1, more preferably between 0.8 and 1.0.

a Nucleophilic Groups

The nucleophilic groups of the first precursor component are able to react with electrophilic groups of the second precursor component. In a preferred embodiment, the electrophilic groups are conjugated unsaturated groups. The nucleophiles that are useful are those that are reactive towards conjugated unsaturated groups via addition reactions, in particular in a self-selective nucleophilic addition reaction under physiological conditions in the human or animal body. The reactivity of the nucleophile depends on the chemical composition and structure of the unsaturated group. Conjugated unsaturated groups are reactive towards water at physiologic pH. Therefore, suitable nucleophiles are those which are more nucleophilic than water at physiologic pH. Preferred nucleophiles are commonly found in biological systems, for reasons of toxicology, but are not commonly found free in biological systems outside of cells.

The suitability of particular nucleophiles depends upon the biomaterial to be formed and the conditions under which it is formed, as well as the amount of self-selectivity desired. In one embodiment, the nucleophile is a thiol. However, amines and/or alkoxides may also be effective nucleophiles.

Thiols are present in biological systems outside of cells in paired form, as disulfide linkages. When the highest degree of self-selectivity is desired (e.g. when the gelation reaction is conducted in the presence of tissue and chemical modification of that tissue is not desirable), thiol can acts as a strong nucleophile.

There are other situations, however, where the highest level of self-selectivity may not be necessary. In these cases, an amine and/or alkoxide may serve as an adequate nucleophile. With respect to amines, particular attention is paid to the pH, in that the deprotonated amine is a much stronger nucleophile than the protonated amine. Thus, for example, the alpha amine on a typical amino acid (pK as low as 8.8 for asparagine, with an average pK of 9.0 for all 20 common amino acids, except proline) has a much lower pK than the side chain epsilon amine of lysine (pK 10.80). As such, if particular attention is paid to the pK of an amine used as the strong nucleophile, substantial self-selectivity can be obtained. By selection of an amine with a low pK, and then formulation of the final precursor such that the pH is near that pK, one can favor reaction of the unsaturation with the amine provided, rather than with other amines present in the system. In cases where no self-selectivity is desired, the pK of the amine used as the nucleophile is less important. However, to obtain reaction rates that are acceptably fast, the pH is adjusted to be the pH of the final precursor solution so that an adequate number of these amines are deprotonated.

The nucleophilic groups may be contained in molecules with great flexibility in overall structure. For example, a difunctional nucleophile could be presented in the form of Nuc-P-Nuc, where P indicates a monomer, oligomer or polymer and Nuc refers to the nucleophile. Likewise, a branched oligomer or polymer, P, can be derivatized with a number of nucleophiles to create P-(Nuc)$_i$, where i is greater than 1. The nucleophile can also be part of the repeating structure, e.g. (P-Nuc)$_i$. Finally, it is not necessary that all of the P and/or the nucleophiles be identical. For example, the precursor component can contain two different nucleophiles, such as amine and thiol.

Preferred First Precursor Components i. Siloxanes

In one embodiment, the first precursor component is a siloxane derivative containing thiols and/or amines as nucleophilic groups. In one embodiment, the cyclosiloxane derivative has the following formula:

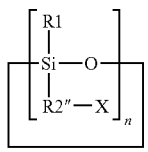

where n=3-6, preferably 4; $R^1$=alkyl, preferably $C_1$-$C_6$-alkyl; and $R^{2''}$=alkyl, preferably $C_2$-$C_3$-alkyl; and X=—SH, —NH$_2$, or combinations thereof.

ii. Cyclohexanes

In another embodiment, the first precursor component is a cyclohexyl-derivative. In one embodiment, the derivative of cyclohexane has the following formula:

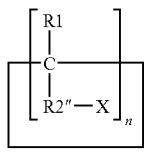

where n=6; $R^1$=H, alkyl preferably $C_1$ to $C_4$, $R^{2''}$=alkyl, preferably $C_1$ to $C_4$ alkyl; and X=—SH, —NH$_2$, or combination thereof. In a preferred embodiment, the derivative of cyclohexane is 1,2,4-Tris(2-mercaptoethyl)-cyclohexane; using the above formula, n=6; $R^1$=H; $R^{2''}$=$C_2H_4$; and X=—SH. (22).

iii. Derivatives of Penaerithritol

In still another embodiment, the first precursor component is a derivative of pentaerythritol containing thiol and/or amine groups. Examples include, but are not limited to, pentaerythritol tetrakis(2-mercaptoproprionate) (26); pentaerythritol tetrakis(3-mercaptopropyl)ether (27); and pentaerythritol tetrakis(mercapto-poly(ethylene glycol) ether) (28).

iv. Derivatives of 1,1,1-Tris-(Hydroxymethyl)Propane

In still another embodiment, the first precursor component is a derivative of 1,1,1, tris-(hydroxy-methyl)propane containing nucleophilic groups, such as thiol and/or amine groups. Examples include, but are not limited to, tri(3-mercaptopropyl)TMP (25).

v. Derivatives of 1,1,1 Tris-(Hydroxy-Methyl)Propanol

In yet another embodiment, the first precursor component is a derivative of 1,1,1 tris-(hydroxy-methyl)propanol containing nucleophilic groups, such as thiol and/or amine groups. Examples include, but are not limited to, 3-(3-mercapto-propoxy)-2,2-bis-(3-mercapto-propoxymethyl)-propan-1-ol (23) and 2-[2,2-Bis-(2-mercapto-ethoxymethyl)-butoxy]-ethanethiol (24).

With respect to i-v, in one embodiment, the first precursor component contains at least two alkyl chains with preferably end-standing thiol and/or amine groups. For example, pentaerithritol, 1,1,1 tris-(hydroxy-methylpropane and 1,1,1 tris-(hydroxy-methyl)propanol can be converted into alkylether or alkylester derivatives containing at least three alkyl-chains with end-standing thiol groups. The length of the alkyl chain and the functionality are determined by the requirement of hydrophobicity, size and intended cross-link density based on the intended use. The length of the alkyl chain also depends on the reaction partner. If the reaction partner is small and compact with a functionality of at least three, the alkyl chains of the pentaerithritol, 1,1,1 tris-(hydroxy-methyl)propane and 1,1,1 tris-(hydroxy-methylpropanol) derivatives can be longer. In one embodiment, the alkyl chain has from 2-10 carbons, preferably from 2-5 carbons.

vi. Silane Derivatives

In still another embodiment, the first precursor component is a silane derivative containing nucleophilic groups, such as thiol and/or amine groups. For example, the silane derivative can have the following formula:

where n is from 2-10, preferably from 2-5 and X is a nucleophilic group as defined above. In one embodiment, n=3 and X is thiol. Examples include, but are not limited to, tetra(3-mercaptopropyl)silane (29).

TABLE 1

Preferred first precursor components

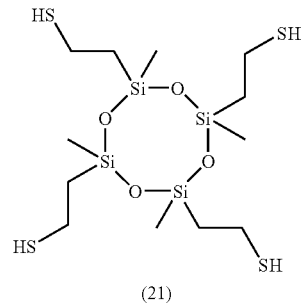

(21)

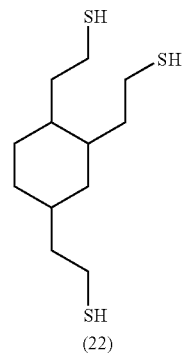

(22)

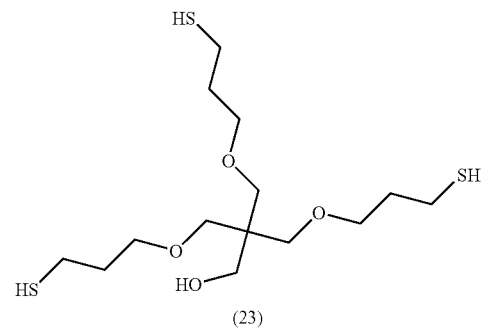

(23)

TABLE 1-continued

Preferred first precursor components (24)

(25)

(26)

C[-O-CH₂CH₂CH₂-SH]₄

(27)

C[-[-O-CH₂CH₂-]ₙ-SH]₄

(28)

Si[-CH₂CH₂CH₂-SH]₄

(29)

b. Electrophilic Groups

The electrophilic groups of the second precursor component are preferably conjugated unsaturated groups. Structures of P and the conjugated unsaturated groups may be similar to those described above for the nucleophiles. It is only necessary that one electrophilic precursor contain greater than or equal to two conjugated unsaturated groups.

It is possible to perform nucleophilic addition reactions, in particular Michael addition reactions, on a wide variety of conjugated unsaturated compounds. In the structures shown below, a monomeric, oligomeric or polymeric structure is indicated as P. Various preferred possibilities for the specific identity of P are discussed below. P can be coupled to reactive conjugated unsaturated groups in structures such as those numbered 1 to 20.

TABLE 2

Molecular structures containing P and conjugated unsaturated groups

1a
X = H, CH₃, CN, COOW
R = H, W, Phenyl-(Ph)
Y = NH, O, 1,4-Ph
W = C1-C5 aliphatic chain 1b
A, Br = H, alkyl
R = H, alkyl
Y = O, NH, 1,4-Ph 2
X = CN, COOW
Y = OW, Ph
W = C1-C5 aliphatic chain

3
X = N, CH

4
A X = CH Y = CH R = H, W-P (W = NH, O, nihil)
B X = N Y = N R = H, P
C X—Y = C═C R = W—P (W = NH, O, nihil)

5

TABLE 2-continued

Molecular structures containing P and conjugated unsaturated groups

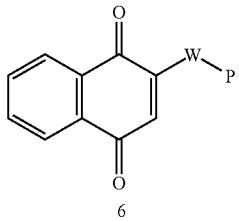
6

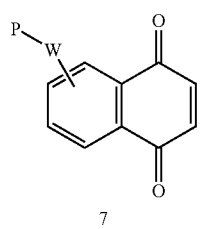
7

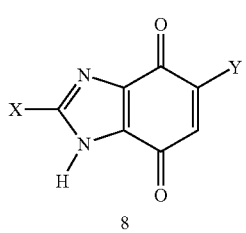
8            X, Y =   H, P
                     P, P
                     P, H
                     P, aliphatic chain

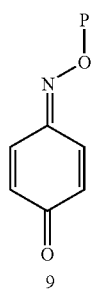
9

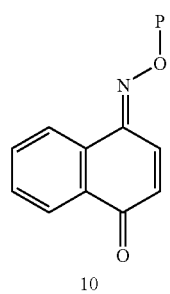
10

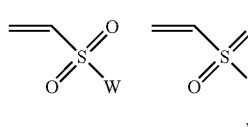
    Y = O, NH
    X = alkali or alkali earth metal ion, P
    W = P, 1,4-Ph-P TABLE 2-continued Molecular structures containing P and conjugated unsaturated groups

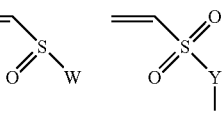
11  12      13  14

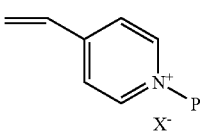
15              X = halogen, sulphonate

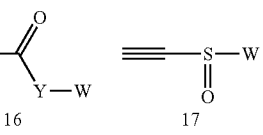
16      17

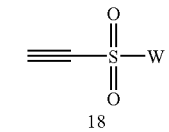
18

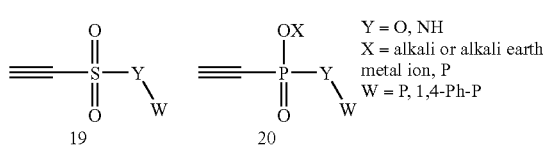
19      20      Y = O, NH
                X = alkali or alkali earth metal ion, P
                W = P, 1,4-Ph-P Reactive double bonds can be conjugated to one or more carbonyl groups in a linear ketone, ester or amide structure (1a, 1b, 2) or to two in a ring system, as in a maleic or paraquinoid derivative (3, 4, 5, 6, 7, 8, 9, 10). In the latter case, the ring can be fused to give a naphthoquinone (6, 7, 10) or a 4,7-benzimidazoledione (8) and the carbonyl groups can be converted to an oxime (9, 10). The double bond can be conjugated to a heteroatom-heteroatom double bond, such as a sulfone (11), a sulfoxide (12), a sulfonate or a sulfonamide (13), or a phosphonate or phosphonamide (14). Finally, the double bond can be conjugated to an electron-poor aromatic system, such as a 4-vinylpyridinium ion (15). Triple bonds can be used in conjugation with carbonyl or heteroatom-based multiple bonds (16, 17, 18, 19, 20).

Structures such as 1a, 1b and 2 are based on the conjugation of a carbon-carbon double bond with one or two electron-withdrawing groups. One of them is always a carbonyl, increasing the reactivity passing from an amide, to an ester, and then to a phenone structure. The nucleophilic addition is easier upon decreasing the steric hindrance, or increasing the electron-withdrawing power in the alpha-position. For example, the following relationship exists, $CH_3 < H < COOW < CN$, where $CH_3$ has the least electron-withdrawing power and CN has the most electron-withdrawing power.

The higher reactivity obtained by using the last two structures can be modulated by varying the bulkiness of the substituents in the beta-position, where the nucleophilic attack takes place; the reactivity decreases in the order P<W<Ph<H. Thus, the position of P can be used to tune the reactivity towards nucleophiles. This family of compounds includes some compounds for which a great deal is known about their toxicology and use in medicine. For example, water-soluble polymers with acrylates and methacrylates on their termini are polymerized (by free radical mechanisms) in vivo. Thus, acrylate and methacrylate-containing polymers have been used in the body in clinical products, but with a dramatically different chemical reaction scheme.

The structures 3-10 exhibit very high reactivity towards nucleophiles, due both to the cis configuration of the double bond and the presence of two electron-withdrawing groups. Unsaturated ketones react faster than amides or imides, due to the stronger electronegativity of these carbonyl groups. Thus, cyclopentendione derivatives react faster than maleimidic ones (3), and para-quinones react faster than maleic hydrazides (4) and cyclohexanones, due to more extended conjugation. The highest reactivity is shown by naphthoquinones (7). P can be placed in positions where it does not reduce the reactivity of the unsaturated group, that is in the opposite part of the ring (3, 5), on another ring (7, 8) or O-linked through a para-quinone mono-oxime (9, 10). To decrease the rate of the nucleophilic addition reaction, P can be also linked to the reactive double bond (6, 8).

The activation of double bonds to nucleophilic addition can be obtained by using heteroatom-based electron-withdrawing groups. In fact, heteroatom-containing analogues of ketones (11, 12), esters and amides (13, 14) provide similar electron-withdrawing behavior. The reactivity towards nucleophilic addition increases with electronegativity of the group. Thus the structures have the following relationship, 11>12>13>14, where 11 is the most electronegative and 14 is the least electronegative. The reactivity towards nucleophilic addition is also enhanced by the linkage with an aromatic ring. A strong activation of double bonds can also be obtained, using electron-withdrawing groups based on aromatic rings. Any aromatic structure containing a pyridinium-like cation (e.g., derivatives of quinoline, imidazole, pyrazine, pyrimidine, pyridazine, and similar $sp_2$-nitrogen-containing compounds) strongly polarizes the double bond and makes possible quick Michael-type additions.

Carbon-carbon triple bonds conjugated with carbon- or heteroatom-based electron-withdrawing groups, can easily react with sulfur nucleophiles, to give products from simple and double addition. The reactivity is influenced by the substituents, in a manner similar to double bond-containing analogous compounds discussed above.

The formation of ordered aggregates (liposomes, micelles) or the simple phase separation in water environment increase the local concentration of unsaturated groups and so the reaction rate. In this case, the latter depends also on the partition coefficient of the nucleophiles, which increases for molecules with enhanced lipophilic character.

Preferred Second Precursor Components

In the preferred embodiment, the second precursor molecule is a monomer, oligomer or polymer that contains acrylates, itaconates, itaconamides, vinylsulfones and/or acrylamides as the conjugated unsaturated group. In particular, the second precursor component may be:

i. Derivatives of 1,1,1 tris(hydroxymethyl)propane containing one or more electrophilic groups, such as conjugated unsaturated groups. Examples include, but are not limited to, trimethylolpropane triacrylate (30); 1,1,1-tris(hydroxymethylpropane-tris(1-n-butyl itaconate) (32); 1,1,1-tris(hydroxymethyl)propane-tris(1-methyl itaconate) (35); and trimethylolpropane tris[poly(propyleneglycol), itaconamide terminated]ether (36);

ii. Derivatives of pentaerythritol containing one or more electrophilic groups, such as conjugated unsaturated groups. Examples include, but are not limited to, pentaerythritol-tetra (1-n-butyl itaconate) (33), pentaerythritol tetrakis(poly(ethylene glycol) acrylate) (37), pentaerythritol tetrakis(2-vinylsulfone-poly(ethylene glycol) ethyl ether) (38), pentaerythritol tetrakis(2-acrylamide-poly(ethylene glycol) ethyl ether) (39), pentaerythritol tetrakis(vinyl sulfone)methyl ether (40), and pentaerythritol tetrakis(3-vinyl sulfone) propyl ether (42);

iii. Derivatives of triglycerol containing one or more electrophilic groups, such as conjugated unsaturated groups. Examples include, but are not limited to, triglycerol-penta(1-methyl itaconate) (31);

iv. Derivatives of bis-pentaerythritol containing one or more electrophilic groups, such as conjugated unsaturated groups, including, but not limited to, dipentaerythritol penta-acrylate (43);

v. Silane derivatives containing one or more electrophilic groups, such as conjugated unsaturated groups, including, but not limited to tetra(3-vinyl sulfone propyl)silane (41);

vi. Ethylene polyamides including, but not limited to, ethylene diamine or triethylene tetraamine, preferably N,N',N'',N'''-tetrakis(1-hydrogen-itaconyl)-triethylenetetramine (34).

The second precursor component contains at least two, preferably three, preferably four, and more preferably five conjugated unsaturated groups, such as acrylates, itaconates, itaconamides, vinysulfones and/or acrylamides.

TABLE 3

Preferred Second Precursor Components

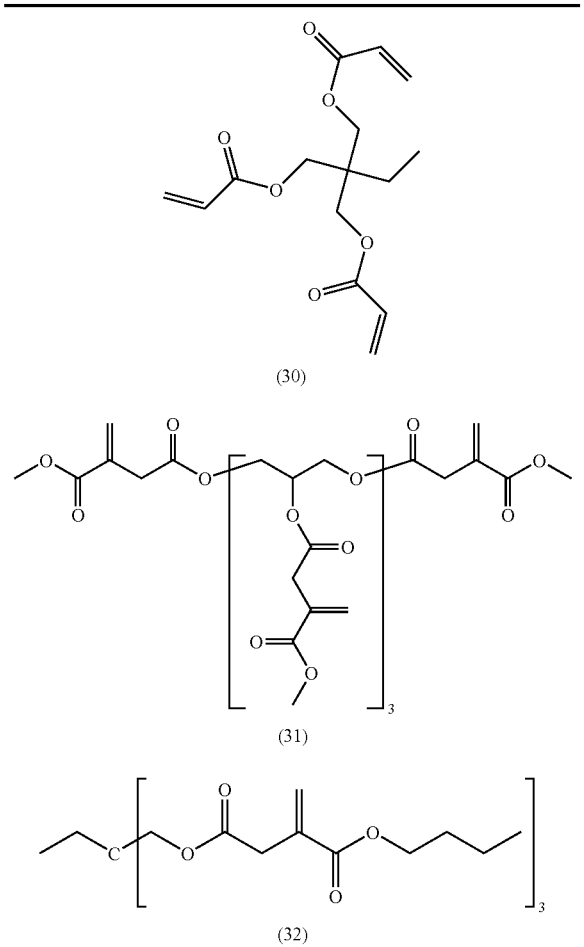

TABLE 3-continued
Preferred Second Precursor Components
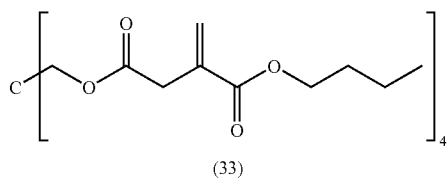
(33)
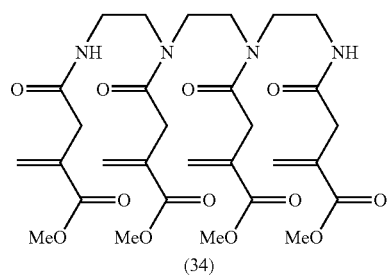
(34)
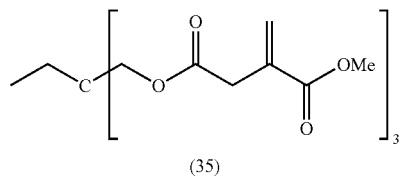
(35)
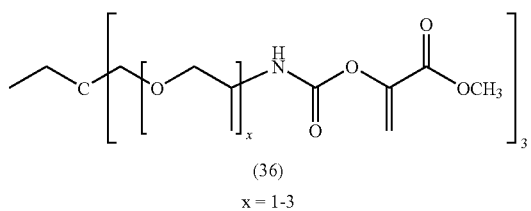
(36)
x = 1-3
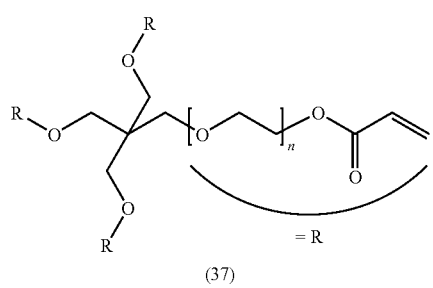
(37)
TABLE 3-continued
Preferred Second Precursor Components
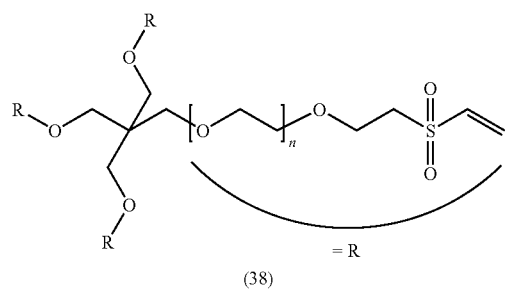
(38)
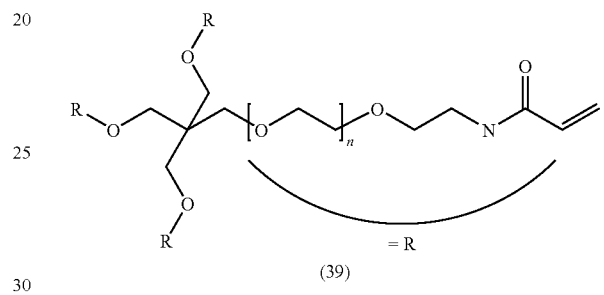
(39)
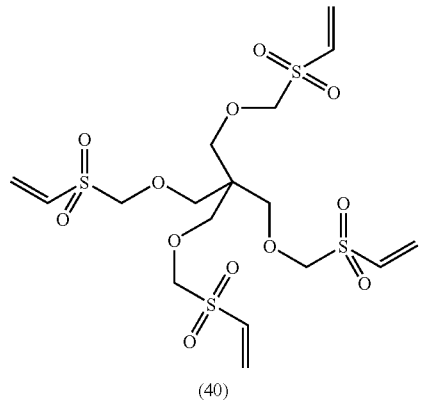
(40)
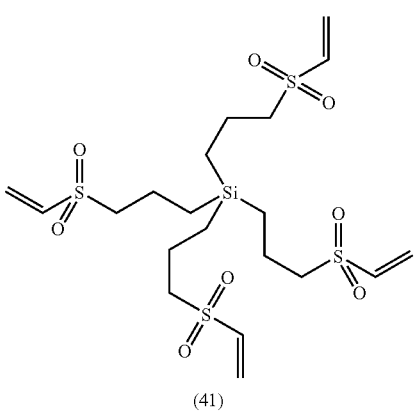
(41)

TABLE 3-continued

Preferred Second Precursor Components

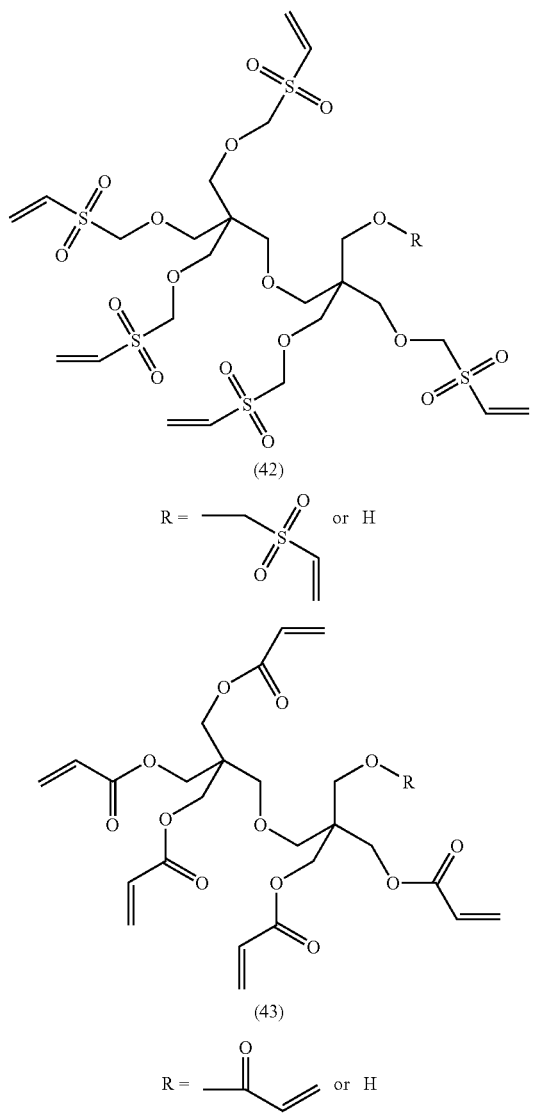

in a preferred embodiment, the second precursor component is dipentaerythritol penta-acrylate (43). In one embodiment, dipentaerythritol penta-acrylate is a mixture of at least tri-, tetra-, penta-, hexa-acrylates, and/or hepta-acrylates, wherein the pentaacrylate is the major component. In still another embodiment, the mixture of acrylates is purified to isolate the penta-acrylate and the purified penta-acrylate is used as the second precursor component.

The preferred composition comprises a first precursor component containing at least tetra(3-mercaptopropyl)silane (29), and a second precursor component containing at least dipentaerythritol penta-acrylate (43). Optionally, this preferred composition further comprises a contrast agent which is preferably $BaSO_4$ Method of Making Second Precursor Component Conjugated unsaturated derivatives of derivatives of 1,1,1 tris(hydroxymethyl)propane, pentaerythritol and triglycerol, such as itaconates, can be synthesized using a variety of methods known in the art. For example, conjugated unsaturated derivatives can be made using the following methodologies:

(A) Two step synthesis via chlorination reaction: saponification of dialkylitaconate to 1-alkyl-4-hydrogen itaconate in the presence of an organic acid, chlorination of 4-hydrogen-1-methyl itaconate to 1-methyl itaconyl chloride with e.g. $SOCl_2$ and reaction of 4-hydrogen-1-methyl itaconate and X—OH(X—OH=1,1,1 tris(hydroxymethyl)propane, pentaerithritol and triglycerol) to form the itaconyl derivatives of X—OH.

(B) Two step reaction via coupling agent: saponification of dialkylitaconate to 1-alkyl-4-hydrogen itaconate in the presence of an organic acid and reaction of 4-hydrogen-1-methyl itaconate with X—OH (X—OH=1,1,1 tris(hydroxymethyl)-propane, pentaerithritol and triglycerol) in the presence of a coupling agent to form the itaconyl derivatives of X—OH (C) One step synthesis via transesterification reaction: reaction between dialkylitaconate and X—OH (X—OH=1,1,1 tris(hydroxymethyl)propane, pentaerithritol and triglycerol) in the presence of e.g. toluene sulfonic acid to form the itaconyl derivatives of X—OH.

In this context, synthesis (B) is preferred.

c. Additives

The composition may further contain at least one thixotropic agent in a range of between 1 to 7 weight % of the total weight of the composition, preferably in a range of between 1.5 to 5 weight % and even more preferably of between 2 to 4 weight %. The thixotropic agent can be organic (e.g. hydroxypropylcellulose) or inorganic, such as hydrophilic or hydrophobic silica, smectite and hormite clay. In a preferred embodiment, hydrophilic silica is used as the thixotropic agent.

The composition can further contain one or more radiopaque agents in order to track the performance of the application and to instantaneously detect potential leakage. The detection of leakage is, especially in vertebroplasty, of importance as described above. The radiopaque agents can be of organic or inorganic nature. In a preferred embodiment, barium sulfate ($BaSO_4$) is used as radiopaque X-ray contrast agent, preferably in a range of between 4 weight % to 80 weight % of the weight of the total composition, preferably in a range of between 10 to 70 weight %, and even more preferably in a range of between 20 to 60 weight %. In one embodiment, the $BaSO_4$ has a specific surface area of greater than or equal to 25 $m^2/g$ and a particle size (diameter) of less than or equal to 100 µm ($d_{50}$). In another preferred embodiment, zirconium oxide ($ZrO_2$) is used as the X-ray contrast agent. Alternatively, strontium containing compounds can be used as contrast agents either alone or as a mixture with other contrast agents. The applicable weight percentages for zirconium oxide and strontium-containing compounds are in the same ranges as for $BaSO_4$.

Whereas the addition of radiopaque agents of a particle size of less than or equal to 100 µm average diameter in an amount of between 4 to 80 weight % of the weight of the total composition gives a uniform radiopaque background under X-ray radiation, the addition of few radiopaque particles of an average diameter of about 250 to 600 µm in addition to the uniform radiopaque background allow detection of not only the injection front, but also the injection behavior within the bulk material. This is known as dynamic imaging. This can serve as a further tool for the instantaneous detection of leakage. In a preferred embodiment, radiopaque particles with an average diameter of about 250 to 600 µm, preferably 500 µm are added to the biomaterial. A preferred particle material is gold or titan.

Apart from their function as thixotropic and X-ray contrast agents, silica, zirconium oxide, strontium-containing compounds, and/or barium sulfate can also serve as fillers in the composition. The addition of fillers can result in an increase/improvement in the mechanical properties (e.g., ultimate compressive strength and Young's modulus E) of the biomaterial compared to the mechanical properties of the polymeric network. For example, the Young's modulus E of a polymeric network of 2,4,6,8-Tetra(2-mercaptoethyl)-2,4,6,8-tetramethylcyclotetrasiloxane and 1,1,1-tris(hydroxymethyl)propane-tris(1-methyl itaconate), in a ratio of the functional groups of 1 (ratio of double bonds to thiol groups), almost doubles by the addition of 25 weight % fillers ($SiO_2$ and $BaSO_4$ and/or $ZrO_2$).

d. Bases

The in situ crosslinking of the first and the second precursor component takes place preferably under basic conditions. A variety of bases comply with the requirements of catalyzing the reaction at physiological conditions (e.g., temperature) and being biocompatible. Tertiary alkyl-amine bases are most suitable in terms of gelation time (preferred is 10 to 15 min) and tolerance for deviation of amount. Suitable bases include, but are not limited to, tributylamine, triethylamine, ethyldiisopropylamine, or N,N-dimethylbutylamine. The most preferred base for forming a biomaterial for hard tissue augmentation and vertebroplasty is tributylamine.

For a given composition, the gelation time is dependant on the amount and type of base. Thus, the gelation time of the composition can be controlled and adjusted to the need of application by varying the base concentration and the type of base. For example, when diethanolamine and ethanolamine are used, the gelation time decreases to 1 to 5 min under comparable conditions. Piperidin, morpholine, triethanolamine, or N-Boc-ethanolamine result in slow gelation times, but they may be used if they are mixed with bases which lead to faster gelation.

e. Solvents

Although compositions are preferred that do not require the presence of solvents, some compositions may require the addition of small amounts of solvents, e.g. for better mixing. In that case, solvents and solvent concentrations are chosen that are not detrimental to the patient.

The first and second precursor components and base, and optionally solvents and/or additives, preferably form a single phase system. The weight % of the sum of donor and acceptor molecules, i.e. the mixture of precursor components, is preferably in a range of between 20 to 95% of the total weight of the composition and even more preferably between 30 and 85 weight %.

III. Biomaterials

The requirements of biomaterials are dependent on the purpose and site of application in the body. In a preferred embodiment, the biomaterial augments hard tissue and is particularly suitable for the use in vertebroplasty. For this purpose, the biomaterial must not be susceptible to swelling and must impart to the tissue in need of augmentation an acceptable mechanical stability after application. The characteristics of the biomaterial are mainly dependent on the choice of the precursor components which crosslink to a polymeric network which forms the basis of the biomaterial. Whereas the mechanical stability of the biomaterial is dependent on the crosslink density of the polymeric network, the water uptake by the biomaterial is influenced by an interplay of the crosslink density, and the hydrophobicity of the polymeric network. For greater crosslink densities and more hydrophobic polymeric networks, the uptake of water by the biomaterial is decreased. Crosslink density and hydrophobic nature of the biomaterial are to a major extent determined by the structure and ratio of the precursor components. Therefore, water-uptake and mechanical performance of the biomaterial can be controlled and influenced by the appropriate choice of the precursor components.

In one embodiment, the uptake of water by the biomaterial should not exceed 7 weight % of the weight of the biomaterial before it is exposed to a storage period of 1 year at 37° C. in water or in a buffer solution (Measured according to ISO 10993-13:1995 (E) in phosphate buffered saline (PBS) 24±2 h after mixing of the precursor components). In the preferred embodiment, the water uptake is less than 5 weight %. In the most preferred embodiment, the water uptake is less than 3 weight %. Preferably each of the precursor components are hydrophobic and slightly soluble in water.

By measurement of Young's modulus E of polymeric networks, information can be obtained with regard to the stiffness of the polymeric network and as such relative information about the crosslink density of the network. The higher the Young's modulus E of a polymeric network, the higher the crosslink density within the network. Young's modulus E of the polymeric network can be increased by addition of additives. such as fillers. Nevertheless, the base value for Young's modulus E is determined by the chemical structure of precursor components and the ratio of their functional groups. After crosslinking, the structure and the ratio are responsible for a certain crosslink density within the polymeric network. Young's modulus E must achieve a predetermined value to be suitable for augmentation of hard tissue and particularly for the use in vertebroplasty.

The precursor components, presence or absence of solvent, and/or base can be varied in order to vary the gelation time of the precursor components. In one embodiment, the gelation time is from about 10 to about 15 minutes. In another embodiment, the gelation time is less than about 10 minutes, preferably less than about 5 minutes, preferably from about 1 to about 5 minutes.

Characteristics of Biomaterials

The ultimate compressive strength (measure for the load bearing capacity) of the biomaterial is in a range of between 7 MPa to 150 MPa, preferably at least 110 MPa. Preferably in a range between 10 MPa and 130 MPa and even more preferably of between 15 MPa to 120 MPa. All of the measurements are taken after storage of the samples at 37° C. for 10 days at a rate of 0.35 mm/s. Preferably the ultimate compressive strength of the biomaterial is 12 MPa after two days storage under dry conditions at 37° C. and reaches at least 5 MPa within the first 4 hours after injection into bone.

Preferably the Young's modulus E of the biomaterial (plus additives) is roughly in the same range as that of trabecular bone.

The precursor components are selected such that they cause Young's modulus E of the polymeric network of the biomaterial to be at least 15 MPa at 10% strain 10 days after mixing, preferably at least 20 MPa and even more preferably at least 25 MPa. Young's modulus E of the biomaterial, also measured after storage of 10 days at 37° C. at 0.35 mm/s and 10% strain, is in the range of between 20 MPa and 160 MPa, preferably in the range of between 60 MPa and 150 MPa and even more preferably in the range of between 60 and 140 MPa.

The injected mixture forms a composite material inside the vertebra. The composites are made of the biomaterial and the spongy tissue. Even a biomaterial with a relatively low Young's modulus E serves its purpose after injection into the spongy tissue. The compressive strength and Young's modulus E are measured according to ISO 5833: 1992 (E).

Biomaterials which show Young's moduli E at around 200 MPa can be used in vertebroplasty. However, the preferred use for such biomaterials is as cementation material, e.g. in joint replacement.

The elongation at break of the biomaterial is preferably in a range of between 20% to 60%, more preferably of between 25% and 55% and even more preferably of between 30% to 40% (storage of biomaterial before measurement 10 days 37° C.).

The biomaterials are stable over a period as set out in the ISO 10993-13:1995 (E), i.e. they do not degrade when stored one year at 37° C. in water or PBS within the margin of error of the respective measurement. At higher temperatures (around 70° C.), the stability of the biomaterial depends to a certain extent on the nature of the conjugated unsaturated group. Biomaterials made from acrylates are more temperature resistant than those made from itaconates, which are more temperature resistant than those made from itaconamides.

III. Methods of Forming Biomaterials

A. Storage

The first and second precursor components are preferably stored under exclusion of oxygen and at low temperatures, e.g. around +4° C., to avoid decomposition of the functional groups prior to use. Preferably the content of functional groups of each precursor component is measured immediately prior to use and the ratio of first and second precursor component (and other precursor component(s), when appropriate) is adjusted according to the predetermined number of the functional groups.

B. Preparation of Composition for Tissue Augmentation

A composition for use as tissue augmentation agent may be prepared by the following general method:

a) providing at least one first multifunctional precursor component comprising at least two nucleophilic groups;

b) providing at least one second multifunctional precursor component comprising at least two electrophilic groups capable of forming covalent linkage with the nucleophilic groups of step a) under physiological conditions;

c) mixing the first precursor component with at least one filler;

d) mixing the second precursor component with at least one filler;

e) filling the mixture obtained in step c) in a delivery device, preferably in a syringe;

f) filling the mixture obtained in step d) in a delivery device, preferably in a syringe.

In another embodiment, a composition for use in tissue augmentation may be prepared by the following general method;

i) providing at least one first multifunctional precursor component comprising at least two nucleophilic groups;

ii) providing at least one second multifunctional precursor component comprising at least two electrophilic groups capable of forming covalent linkages with the nucleophilic groups of step a) under physiological conditions;

iii) mixing the first precursor and the second precursor components;

iv) adding a base to the mixture of the first and second precursor component and mixing;

v) adding a filler to the mixture of the first and second precursor component, mixing and allowing the precursor components to complete crosslinking.

The first and second precursor components and the fillers are sterilized prior to mixing. This preferably is done by sterile filtration of the precursor components and gamma irradiation of the fillers. The mixtures obtained in steps e), f) and iii) can be stored over a prolonged time, preferably at low temperatures.

Immediately prior to application, the contents of the delivery devices obtained in step e), f) and iii) are mixed with one another and secondly with a predetermined amount of sterilized base. A predetermined amount of base is filled in a delivery device, preferably another syringe. Tertiary alkylamine bases are most suitable in terms of gelation time preferred gelation time is 10 to 15 min) and tolerance for deviation of amount. Preferably the bases are tributylamine, triethylamine, ethyldiisopropylamine, or N,N-dimethylbutylamine. The most preferred base for forming a biomaterial for hard tissue augmentation and vertebroplasty is tributylamine.

There are different modes of mixing the components. In one embodiment, three syringes, one containing the nucleophilic precursor, another containing the electrophilic precursor, and the third containing a base, can be interconnected using a three-way connector device. The contents of the syringes are mixed by being squeezed through a static mixture at the outlet of the three way connector device. The mixed components are injected directly at a site in need of treatment in the body by connecting the static mixer to an injection needle. Alternatively, the mixture is squeezed into another syringe which then is connected to the injection needle.

In a second embodiment, the mixture containing the electrophilic precursor, obtained in step d), is mixed with the base. This is preferably done by connecting the syringe containing the base to the syringe containing the electrophilic precursor through a connector device, which allows for syringe-to-syringe mixing of the respective contents. A static mixer may be part of the connector device. The mixing is complete when homogenous mixing is achieved, which optionally may be made noticeable by adding biocompatible coloring agents to the base and/or the mixture obtained step d). After mixing, one syringe contains a mixture of the base/second precursor/filler and the other syringe is empty. Then, the empty syringe is removed from the connector device and replaced by the syringe containing the nucleophilic precursor. Again, syringe-to-syringe mixing is one way to achieve homogeneous mixing of both contents. Subsequently the syringe containing the mixture is connected to the injection needle and the mixture is injected at the site of need in the body.

Alternatively, the syringe containing the base/second precursor/filler mixture and the syringe containing the first precursor/filler mixture, are interconnected through a two-way connector device comprising a static mixer at its outlet. The two-way connector device can be a double compartment syringe. The contents are mixed by squeezing the contents of the syringes through the static mixer. The static mixture is either directly connected to the injection needle or the mixture is squeezed in a further syringe, which then is connected to the injection needle.

C. Mixture of Precursor Components

The precursor component mixture has thixotropic properties. Thus it flows when subject to pressure, but recovers, nearly instantaneously, its original viscosity once pressure is removed. When a surgeon detects leakage from the vertebra by X-ray analysis during injection he/she immediately stops pressing the plunger of the syringe, and as a result the mixture stops flowing. Injection will be continued at another location in the vertebra (usually several needles are inserted into one vertebra prior to injection). The material starts being injectable upon a pressure of 4 Pa, preferably however at a higher pressure, such as around 10 Pa.

The mixture is of low viscosity prior to reaching the gel point so that the mixture flows, penetrates and distributes easily and evenly inside the spongy part of the vertebra.

D. Crosslinking Reaction Between Nucleophilic and Electrophilic Groups

After injection, the mixed precursor components crosslink (thus harden) within the next two to four hours to such an extent that the biomaterial can withstand loads to the extent that the patient can stand up and walk. The viscosity profile of the biomaterial takes these requirements into account in that the viscosity only increases slightly the first eight to fifteen minutes after mixing of the precursor components (before reaching the gel point) and then increases exponentially after that. The precursor mixture reaches its gel point at around eight to fifteen minutes, preferably at around twelve minutes. This gives the surgeon sufficient time for the operation. The biomaterial reaches its ultimate strength within 10 days, preferably 5 days after mixing.

The crosslinking of the first and second precursor component at the site of application is associated with only moderate exothermicity. The tissue at the site of application is much less harmed by injection of the composition than by injection of PMMA.

Michael-Type Reaction

The first and the second precursor components preferably react by a 1,4 addition reaction of a nucleophile on a conjugate unsaturated system. This reaction is referred to as a Michael-type reaction or Michael addition reaction. The reaction mechanism could be purely polar, or proceed through a radical-like intermediate state(s). Lewis acids or bases or appropriately designed hydrogen bonding species can act as catalysts.

Michael-type addition to conjugated unsaturated groups can take place in substantially quantitative yields under physiological conditions (e.g., temperatures), in particular at body temperature but also at lower and higher temperatures. They take place in mild conditions with a wide variety of nucleophiles. The gel formation kinetics and the mechanical and transport properties of the product are tailored to the needs of the application.

Compared to the preparation of PMMA in the operating room, it is evident that preparation and handling of this composition is faster, reproducible, more precise, and avoids health hazards for the people responsible for preparation of the mixture.

IV. Kits for Forming In Situ Crosslinkable Compositions

A kit containing at least a first and a second precursor component. The kit may also contain one or more devices, such as syringes, for administering the first and second components. The kit may contain a base for polymerizing the precursor component. Optionally, the first and/or the second precursor component(s) contain one or more additives and/or biologically active agents. The precursor components may be placed in the one or more devices prior to administration to a patient. The kit can also contain instructions for preparing the precursor components and/or additives as well as mixing the precursor components and additives to form the biomaterial.

V. Uses for the Compositions

The multifunctional precursor components are selected and tailored to produce biomaterials with the desired properties. The precursor components are capable of in situ crosslinking at physiological temperature, to specific augmentation requirements. In the preferred embodiment, the biomaterials are used to augment hard tissues, such as bone.

The biomaterial can be utilized in a wide variety of orthopedic, periodontal, and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, intermaxillary fixation of fractures, mentoplasty, temporomandibular joint replacement, inlay osteoimplants, implant placement and revision, and combinations thereof. However, the precursor components can also be tailored to produce biomaterials that are suitable for other types of tissue augmentation.

A. Hard Tissue Augmentation and Vertebroplasty

In the preferred embodiment, the in situ crosslinkable composition forms a biomaterial for augmenting hard tissue. In particular, the biomaterial may be used to augment at least one vertebra of the spine. The composition contains at least a first and a second precursor component. In one embodiment, the first precursor component is a thiolated cyclosiloxane derivative, and the second precursor component contains at least three acrylate groups and is a derivative of 1,1,1 tris (hydroxymethyl)propane, pentaerithritol, or triglycerol.

In a preferred application, the composition is used in vertebroplasty. The composition used in vertebroplasty contains at least a first precursor component comprising tetra(3-mercaptopropyl)silane (29), and a second precursor component comprising dipentaerythritol penta-acrylate (43). Preferably, the composition further contains BaSO4. Preferably the ratio of the number of the functional groups in the two precursor components is from 0.8 to 1.1, and most preferably the ratio is between 0.9 and 1.0. Another preferred composition contains at least a first precursor component containing 2,4,6,8-Tetra(2-mercaptoethyl)-2,4,6,8-tetramethylcyclotetrasiloxane (21), and a second precursor component containing trimethylolpropane triacrylate (30). Although additional components with electrophilic and/or nucleophilic groups can be included in the composition, the best results are obtained if the two components are used alone. Preferably the ratio of the number of the functional groups in the two precursor components is from 0.8 to 1.1, and most preferably the ratio is between 0.9 and 1.0.

Alternatively, the first precursor component is pentaerythritol tetrakis(2-mercaptoproprionat) (26), and the second precursor component is trimethylolpropane triacrylate (30). The ratio of the number of the functional groups in the two precursor components is about 1.

Other suitable compositions for vertebroplasty and hard tissue augmentation contain a thiolated cyclosiloxane derivative, in particular 2,4,6,8-Tetra(2-mercaptoethyl)-2,4,6,8-tetramethylcyclotetrasiloxane (21), as the first component, and a molecule containing itaconate or itaconamide groups, in particular N,N',N'',N'''-tetrakis(1-hydrogen-itaconyl)-triethylenetetramine (34), itaconate derivatives of 1,1,1 tris(hydroxymethyl)propane and tri glycerol molecules, and mixtures thereof, as the second component. Preferably, the second component is 1,1,1-tris(hydroxymethyl)propane-tris (1-methyl itaconate) (35), Triglycerol-penta(1-n-butyl itaconate) (31), 1,1,1 tris(hydroxymethyl)propane-tris(1-n-butyl itaconate) (32), or Pentaerithritol-tetra(1-n-butyl itaconate) (33).

B. Medical Indications Other than Hard Tissue Augmentation and Vertebroplasty

Tissue augmentation is one of the possible treatments for urinary incontinence in women, There the biomaterial is placed at the base of the bladder to provide sphincter support by enhancing urethal compression. For such applications, the biomaterial must be softer and more elastic than the biomaterials used in hard tissue augmentation. For example, the Young's modulus E should range between 0.5 MPa to 4 MPa at 10% strain and 0.35 mm/s. In contrast to treatments for hard tissue, the prevention of swelling is not important because the surrounding tissue can stretch more than hard tissue, but biomaterials that swell too much will not be acceptable even for soft tissue applications. Thus, for soft tissue applications, such as the treatment of urinary incontinence, the up-take of water by the biomaterial should not exceed 20 weight %.

a. Modifications to First and Second Precursor Components

Although the biomaterials as described herein lose some of their stiffness simply due to the fact that an X-ray contrast agent is not needed any longer (the operation is done under camera control) the combination of the precursor components often leads to polymeric networks and biomaterials which are too stiff and hard for soft tissue applications. Therefore for treatments of soft tissue, at least one of the first or second precursor components should to be replaced by a molecule which by its structure and functionality leads to softer biomaterials. In one embodiment, the second precursor molecule is modified to comply with the needs of urological bulking whereas the first precursor component remains unaltered (i.e. the first precursor is the same as the first precursor used in hard tissue augmentation). Alternatively, the first precursor component is modified and the second precursor remains unaltered (i.e. the second precursor is the same as the second precursor used in hard tissue augmentation).

In a preferred embodiment the second precursor component is a derivative of polypropylene that contains two conjugated unsaturated groups. Particularly preferred are diacrylate polypropylene, such as polypropylene oxide diacrylate with n=12 (44), diitaconamide polypropylene, such as polypropylene α,ω bis(1-propylene itaconamide) with n=6 or 300, acrylamide polypropylene, such as polypopyleneoxide α,ω bis(1-propylene itaconamide) (46) and derivatives thereof.

In a preferred embodiment, a biomaterial for soft tissue augmentation is formed from at least a first precursor component, which is a multifunctional thiolated cyclohexane derivative, mercaptoalkylether of pentaerithritol, 1,1,1 tris-(hydroxy-methyl)propane and 1,1,1 tris-(hydroxy-methyl) propanol containing at least three alkylether chains with endstanding thiol groups and at least a second precursor component, which is diacrylate-, diacrylamide- or diitaconamide polypropylene or derivatives thereof. In particular, such a biomaterial could be used for urological bulking.

b. Additives

The composition may also contain thixotropic agents, such as silica, to prevent leakage and uncontrolled flow in a range of between 0.1 to 110% weight percent of the total weight of the composition, preferably in a range of between 1 to 5 weight % and even more preferably between 1.5 and 3 weight %.

The compositions may also contain bioactive factors, which can diffuse slowly from the biomaterial and thus helping the tissue to regenerate and heal. In such cases, the biomaterial works as both an augmentation material composition and as a drug delivery matrix. The bioactive factors may be growth factors, preferably those from the TGF beta superfamily, PTH and PDGF.

c. Characteristics of Biomaterials for Soft Tissue Augmentation

The Young's modulus E of the compositions for soft tissue applications is between 0.5 and 4 MPa, and the gel point is between 20 and 40 min. The gel point is important since the injection of the material cannot be done as quickly as in vertebroplasty. The biomaterial has a water uptake of under 20% of the total weight of the composition. The biomaterial is stable for at least 1 year at 37° C. At higher temperatures the itaconamides and itaconates tend to be more stable than the acrylates.

TABLE 4

Modified Second Precursor Components for Soft Tissue Applications

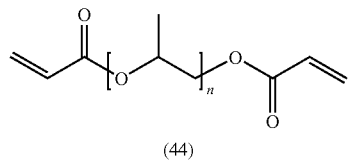

(44)

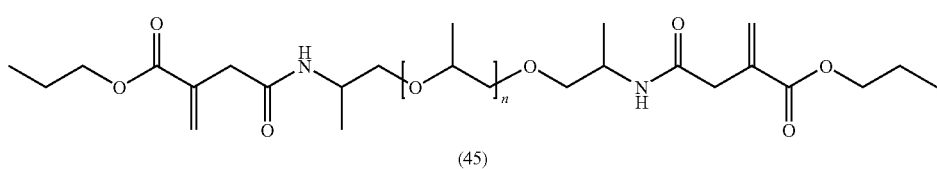

(45)

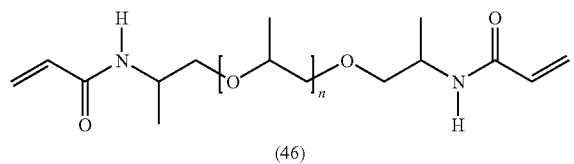

(46)

The molecular weight of the molecules are preferably in a range of between 800 and 3000 g/mol, preferably of between 900 and 2600 g/mol and even more preferably of between 1200 and 2400 g/mol.

Other augmentation applications are possible as e.g. in cosmetic surgery. For example, the biomaterial can be made softer by further increasing the length of the alkyl chains of one of the precursor components or by using first and second precursor components which both have increased chain length and thus are made suitable for wrinkle augmentation.

EXAMPLES

Measurements

|  | Instrument | Parameter |
|---|---|---|
| Viscosity | Bohlin Instruments CVO 120 | Stress ramp: 0.1 Pa to 100 Pa at 25° C. |
| Gel point | Bohlin Instruments CVO 120 | Frequency: 1 H; Temperature: 37° C.; Strain: 0.1; Initial stress 0.1 Pa; Gap: 100 μm; continuous oscillation |
| Compression strength + Young's modulus E | ASTM F-451-99a; MTS Synergie 100 (1 kn-cell) | if not indicated otherwise: velocity: 0.35 mm/s; maximal force: 950 N; sample size: 12 mm height, 6 mm diameter; Measurement of force and deformation; Calculation of stress = force/area, strain = ΔL/L, E = stress/strain. |

Example 1

Synthesis of 1,1,1-tris(hydroxymethyl)propane-tris(1-methyl itaconate)

A. Two Step Synthesis Via Coupling Agent

Three different procedures may be used in the first step of this synthesis.

Step 1: 4-hydrogen-1-methyl itaconate (first possibility)

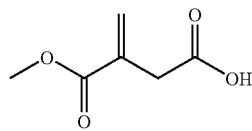

50.7 g (0.32 mol) of dimethyl itaconate and 25.0 g (0.13 mol) of toluene-4-sulfonic acid monohydrate were dissolved in 25 ml of water and 180 ml of formic acid in a 500 ml round bottom flask, equipped with a reflux condenser and a magnetic stirring bar. The solution was brought to a light reflux by immersing the flask in an oil bath at 120° C. and was stirred for 15 min. Then, the reaction was quenched by pouring the slightly yellow, clear reaction mixture into 200 ml of ice water while stirring. The resulting clear aqueous solution was transferred to a separation funnel, and the product was extracted with six 100 ml portions of dichloromethane. The combined organic layers were dried over $Na_2SO_4$, and the solvent was removed by rotary evaporation, yielding 22.2 g (44.8%) of raw product. The raw product was distilled under reduced pressure, yielding 11.7 g of a clear and colorless oil. According to $^1$H NMR analysis, the product consisted of 4-hydrogen-1-methyl itaconate (92%), 1-hydrogen-4-methyl itaconate (ca. 3%), and dimethyl itaconate (ca. 5%). See H.-Z. Pan, Y. Yan, L. Tang, Z.-Q. Wu, F.-M. Li, *Macromol. Rapid Commun.* 21, 567-573 (2000)

Step 1: 4-hydrogen-1-methyl itaconate (second possibility)

102.1 g (0.65 mol) of dimethyl itaconate and 35.0 g (0.18 mol) of toluene-4-sulfonic acid monohydrate were dissolved in 50 ml of water and 250 ml of formic acid in a 1000 ml round bottom flask, equipped with a reflux condenser, a thermometer, and a magnetic stirring bar. The solution was brought to a light reflux by immersing the flask in an oil bath at 120° C. and was stirred for 45 min. Then, the reaction was quenched by pouring the slightly yellow, clear reaction mixture into 300 g of ice while stirring. The resulting clear aqueous solution was transferred to a separation funnel and the product was extracted with three 200 ml portions of dichloromethane. The combined organic layers were dried over $MgSO_4$, and the solvent was removed by rotary evaporation, yielding 64.5 g of raw product. Extracting the aqueous layer once more with 200 ml of dichloromethane yielded another 6.4 g of raw product. A typical acidic smell indicated the presence of some formic acid in the fractions, which was removed by dissolving the combined fractions in 150 ml of dichloromethane and washing twice with 50 ml of saturated aqueous NaCl solution. Drying the organic layer with $MgSO_4$ and evaporating the solvent yielded 60.1 g of a clear and colorless oil, which was distilled under reduced pressure, yielding 55.3 g of a clear and colorless oil. According to $^1$H NMR analysis the product consisted of 4-hydrogen-1-methyl itaconate (91%), 1-hydrogen-4-methyl itaconate (ca. 5%), and dimethyl itaconate (ca. 4%).

Step 1: 4-hydrogen-1-methyl itaconate (third possibility)

176 g (1.15 mol) of dimethyl itaconate were dissolved in 90 ml of water and 318 ml of formic acid and the mixture was heated to 60-65° C. and stirred at reduced pressure (300-250 mbar) for 4 days. After four days, GC analysis showed a conversion of 71.5%. Then, the pressure was reduced to 200-100 mbar and 170 ml of solvent was distilled off The reaction mixture was cooled to 20° C., diluted with 350 ml water and 710 ml saturated aqueous NaCl solution, and extracted with three 350 ml portions of dichloromethane. The combined organic layers were concentrated to 15% of their original volume and 1.06 l of saturated aqueous $NaHCO_3$ solution was added while stirring. The organic layer containing 28.7 g of unreacted dimethyl itaconate was discarded, and the aqueous layer was extracted with three 350 ml portions of dichloromethane, removing another 3.5 g of unreacted dimethyl itaconate. The aqueous layer was reacted with 140 ml of 32% aqueous HCl and extracted with three 350 ml portions of dichloromethane, which, upon evaporation of the solvent, yielded 89.8 g (55%) of 4-hydrogen-1-methyl itaconate in 98.3% purity (GC).

Step 2: 1,1,1-tris(hydroxymethyl)propane-tris(1-methyl itaconate) (35)

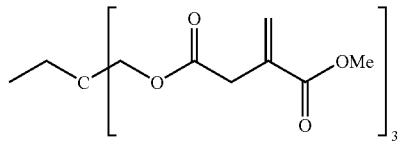

75.0 g (0.39 mol) of N-(3-dimethylaminopropyl)-N'-ethylcarbodiimide hydrochloride was suspended in 300 ml of dichloromethane and 10.47 g (0.078 mol) of 1,1,1-tris-(hydroxymethyl)-propane and 0.95 g (7.8 mmol) of 4-(dimethylamino)-pyridine were added. After evacuating the reactor and flushing with nitrogen, the suspension was cooled to 2° C. and 56.0 g (0.39 mol) of 4-hydrogen-1-methyl itaconate dissolved in 100 ml of dichloromethane was added at such a rate that the temperature of the reaction mixture remains <5° C. Then, the solution, which had become clear, was stirred overnight and extracted with two 300 ml portions of saturated aqueous NaHCO$_3$ solution, two 300 ml portions of 1 M hydrochloric acid, and with 300 ml of water. Colored byproducts were removed by a plug filtration over 40 g of silica gel and the solvent was evaporated, yielding 37.2 g of the desired product as an orange oil. Column chromatography over silica gel afforded the pure product was as a pale yellow oil. Molecular weight 512.54; 5.85 meq/g C=C B. Two Step Synthesis Via Chlorination Step 1: 4-hydrogen-1-methyl itaconate See synthesis of Step 1 described above.

Step 2: 1-methyl itaconyl chloride

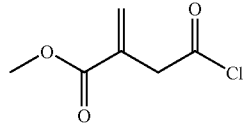

7.14 g (46 mmol) of 4-hydrogen-1-methyl itaconate were weighed into a 50 ml two-neck round bottom flask, equipped with a reflux condenser, a septum and a magnetic stirring bar. 5 ml of dry diethyl ether, 1 drop of pyridine and 5 ml (69 mmol) of thionyl chloride were added. The resulting solution was brought to reflux and stirred for 15 min. Then the oil bath was removed and a light argon stream was led through the reaction mixture in order to remove HCl and SO$_2$. The last traces of these gases and the solvent were removed by distillation under membrane pump vacuum. The resulting yellow oil was distilled under reduced pressure. A clear and colorless oil distilled at 66-68° C./8-9 mbar. The IR spectrum showed carbonyl bands for a saturated acid chloride (1804 cm$^{-1}$) and a conjugated ester (1724 cm$^{-1}$). $^1$H NMR analysis showed the product to consist of 1-methyl itaconyl chloride (89%), 4-methyl itaconyl chloride (ca. 4%), and dimethyl itaconate (ca. 7%). See H.-Z. Pan, Y. Yan, L. Tang, Z.-Q. Wu, F.-M. Li, Macromol. Rapid Commun. 21, 567-573 (2000).

Step 3: 1,1,1-tris(hydroxymethyl)propane-tris(1-methyl itaconate) (35)

2.64 g (19.7 mmol) of 1,1,1-tris(hydroxymethyl)propane was dissolved in 20 ml of dry 1,4-dioxane and 55 ml of dry dichloromethane were added. The solution was cooled with an ice bath and 10.4 g (64.1 mmol) of 1-methyl itaconyl chloride in 5 ml of dry dichloromethane were added dropwise in 2 min. and the mixture was stirred for 10 min. Then, 7.10 g (70.2 mmol) triethylamine dissolved in 20 ml of dry dichloromethane were added at such a rate that the temperature of the reaction mixture remained below 5° C. (ca. 45 min.). After addition was complete, stirring was continued for 1 hr., after which the ice bath was removed and the reaction mixture brought to a mild reflux and was stirred for another hour. Then the ammonium salts were removed by filtration over ca. 1 cm of neutral Al$_2$O$_3$ and the solvents were rotavaped off the filtrate. The oil was dissolved in diethyl ether and washed with 50 ml of 3% aqueous HCl, twice with 50 ml of saturated aqueous NaHCO$_3$, and once with 50 ml of water. The organic layer was dried with MgSO$_4$ and the solvent was removed by rotary evaporation and 18 mg of MEHQ were added. The resulting greenish brown, clear oil was purified by column chromatography over silica gel (column height ca. 45 cm, ø5 cm, eluent hexane/ethyl acetate 1/1 @ 16-18 ml/min.) The product was recovered as a pale yellow oil, yield 5.49 g (55%).

C. One Step Synthesis Via Transesterification; Synthesis (C)

1,1,1-tris(hydroxymethyl)propane-tris(1-methyl itaconate) (35)

7.14 g (0.053 mol) of 1,1,1-tris(hydroxymethyl)propane, 30.03 g (0.190 mol) of dimethyl itaconate, 9.19 g (0.048 mol) of toluene-4-sulfonic acid monohydrate, and 56 mg of 2,6-di-tert-butyl-p-cresol were weighed into a 100 ml round bottom flask, equipped with a Dean Stark trap. The flask was heated to 100° C. and methanol was distilled off under reduced pressure. After 6 hrs. the reaction mixture was dissolved in 25 ml of toluene and the volatiles were removed by rotary evaporation. The resulting clear, amber colored mixture was poured into 60 ml of 1 M aqueous NaHCO$_3$ and 100 ml of diethyl ether were added to dissolve the product. The organic layer was washed with 60 ml of 1 M aqueous NaHCO$_3$ and 60 ml of water, dried with Na$_2$SO$_4$ and the solvent was removed by rotary evaporation, yielding 27.5 g (86%) of raw product. 14.3 g of the raw product were purified by column chromatography over Silicagel 60 with 2/1 hexane/ethyl acetate as eluent. After the excess of dimethyl itaconate had eluted, the eluent was changed for a 1/1 hexane/ethyl acetate mixture and 4.48 (31%) of 1,1,1-tris(1-methyl-itaconoxymethyl)propane were recovered.

Example 2

Synthesis of Triglycerol-penta(1-methyl itaconate) (3)

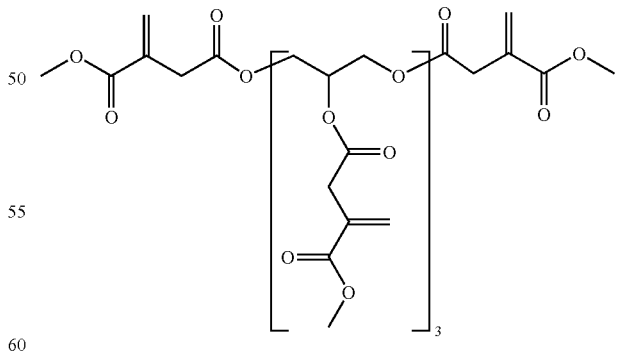

1.25 g (5.2 mmol) of triglycerol, 5.41 g (36.0 mmol) of 4-hydrogen-1-methyl itaconate, and 0.45 g (3.6 mmol) of 4-(dimethylamino)-pyridine were dissolved under an Ar atmosphere in 20 ml of dry chloroform and cooled to 1° C. 7.09 g (36.9 mmol) of N-(3-dimethylaminopropyl)-N-ethyl-carbodiimide hydrochloride was dissolved in 40 ml of dry chloroform and added dropwise at such a rate that the temperature of the reaction mixture remains <5° C. Then the reaction mixture was allowed to slowly warm up to room temperature and stirred overnight. The resulting clear, yellow solution was washed with 50 ml of saturated aqueous NaHCO$_3$ solution, 50 ml of 1 M aqueous KHSO$_4$ solution, 50 ml of saturated aqueous NaHCO$_3$ solution, and 50 ml of saturated aqueous NaCl solution, dried over MgSO$_4$, and filtered over ca. 3 cm of silica gel and Celite 545. Evaporation of the solvents yielded 2.56 g (57%) of the desired product. IR analysis confirmed the complete conversion of the OH groups. M=870.78; 5.74 meq/g C=C.

Example 3

Synthesis of 1,1,1-tris(hydroxymethyl)propane-tris(1-n-butyl itaconate)

Step 1: 4-hydrogen-1-n-butyl itaconate

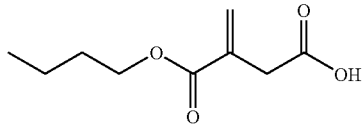

104.7 g (0.43 mol) of di-n-butyl itaconate and 3.93 g (0.021 mol) of toluene-4-sulfonic acid monohydrate were dissolved in 140 ml of formic acid in a 500 ml round bottom flask, equipped with a reflux condenser, a thermometer, and a magnetic stirring bar. 30 ml of water were added and the resulting solution was heated to 66° C. by immersing the flask in an oil bath at 72° C. and was stirred at that temperature for 48 hrs. Then, the reaction was quenched by pouring the slightly yellow, clear reaction mixture into 600 ml of ice water while stirring. The resulting light yellow emulsion was transferred to a separation funnel and the product was extracted by washing three times with 200 ml of dichloromethane. The combined organic layers were washed with 100 ml of saturated aqueous NaCl solution and dried over Na$_2$SO$_4$. Removal of the solvent by rotary evaporation yielded 75.3 g of raw product. According to $^1$H NMR analysis the raw product consisted for 81% of 4-hydrogen-1-n-butyl itaconate, for ca. 4% of 1-hydrogen-4-n-butyl itaconate, and for ca. 15% of di-n-butyl itaconate. To the raw product 250 ml of saturated aqueous NaHCO$_3$ solution and 17.6 g of NaHCO$_3$ were added, yielding a hazy, red solution, which was washed 3 times with 100 ml of diethyl ether. To the clear, red aqueous layer KHSO$_4$ was added until the pH has dropped from 8.5 to 3.0 and it was washed twice with 100 ml of dichloromethane. Then more KHSO$_4$ was added until the pH value is 2.2 and the solution was washed again twice with 100 ml of dichloromethane. The yellow organic layer was washed with 50 ml of saturated aqueous NaCl solution and dried over MgSO$_4$. Evaporating the solvent yielded 53.6 g (67%) of a clear, yellow oil, which, according to $^1$H NMR analysis, consisted for 95% of 4-hydrogen-1-n-butyl itaconate and for ca. 5% of 1-hydrogen-4-n-butyl itaconate.

Step 2: 1,1,1-tris hydroxymethyl)propane-tris(1-n-butyl itaconate) (32)

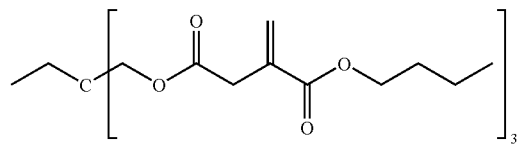

2.00 g (14.9 mmol) of 1,1,1-tris-(hydroxymethyl)-propane, 11.3 g (59.0 mmol) of N-(3-dimethylaminopropyl)-N'-ethylcarbodiimide hydro-chloride, and 0.43 g (3.5 mmol) of 4-(dimethylamino)-pyridine were suspended in 150 ml of dry dichloromethane under an Ar atmosphere. The suspension was cooled to 1° C. and 9.65 g (51.8 mmol) of 4-hydrogen-1-n-butyl itaconate dissolved in 80 ml of dry dichloromethane were added dropwise at such a rate that the temperature remains below 2° C. After complete addition the clear, yellow reaction mixture was allowed to warm up to room temperature and stirred for another hour. After filtration and removal of the solvent, 100 ml of diethyl ether were added and the solution was washed with 50 ml of saturated aqueous NaHCO$_3$ solution, 50 ml of 3% hydrochloric acid, and 25 ml of saturated aqueous NaHCO$_3$ solution with 25 ml of water. Drying the organic layer with MgSO$_4$ and evaporation of the solvent yielded 7.93 g (80%) of the product as a reddish brown oil. Molecular weight 638.75 g/mol; 4.70 meq/g.

Example 4

Synthesis of Pentaerythritol-tetra(1-n-butyl itaconate) (33)

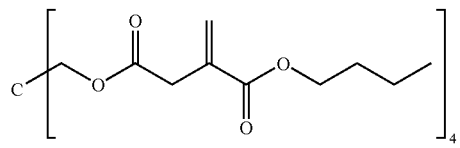

1.53 g (11.2 mmol) of pentaerythritol, 12.0 g (62.8 mmol) of N-(3-dimethylaminopropyl)-N'-ethylcarbodiimide hydrochloride, and 0.45 g (3.7 mmol) of 4-(dimethylamino)-pyridine were suspended in 100 ml of dry dichloromethane under an Ar atmosphere. The suspension was cooled to 1° C. and 10.0 g (53.9 mmol) of 4-hydrogen-1-n-butyl itaconate dissolved in 40 ml of dry dichloromethane were added dropwise at such a rate that the temperature remained below 2° C. After complete addition the clear, yellow reaction mixture was allowed to warm up to room temperature in about one hour. Then the solvent was evaporated, 100 ml of diethyl ether were added and the solution was washed with 50 ml of saturated aqueous NaHCO$_3$ solution, 50 ml of 1.0 M aqueous KHSO$_4$ solution, 40 ml of saturated aqueous NaHCO$_3$ solution with 10 ml of water, and 50 ml of water. Drying the organic layer with Na$_2$SO$_4$ and evaporation of the solvent yielded 9.81 g (103%) of the desired product as a clear, brown oil. Molecular weight=880.92 g/mol; 4.54 meq/g C=C

Example 5

Synthesis of N,N',N'',N'''-tetrakis(1-methyl-itaconyl)-triethylenetetramine (34)

Step 1: N,N',N'',N'''-tetrakis(1-hydrogen-itaconyl)-triethylenetetramine

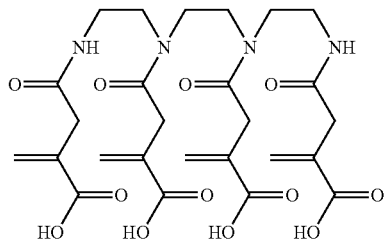

3.30 g (22.6 mmol) of triethylenetetramine were dissolved in 200 ml of water and the solution was cooled in an ice bath. Under vigorous stirring 18.73 g (167 mmol) of itaconic anhydride dissolved in 50 ml of dichloromethane were added dropwise in 90 min., at such a rate that the temperature remained between 4 and 6° C. During addition the pH of the reaction mixture was kept at 9.5 by addition of 4 M aqueous NaOH. After addition was complete, the reaction mixture was transferred to a separation funnel and the layers were separated. The aqueous layer was acidified with concentrated hydrochloric acid (pH 2), washed with 100 ml of dichloromethane and left standing at 4° C. to crystallize. The crystalline material was filtered off and dried under vacuum. Yield: 5.46 g (41%).

Step 2: N,N',N'',N''',N''''-tetrakis(1-methyl-itaconyl)-triethylenetetramine (32)

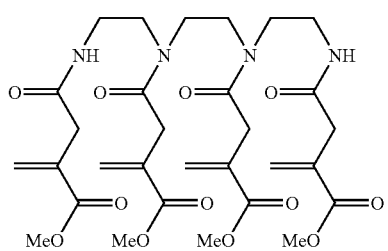

5.4 ml (74 mmol) of thionylchloride were added slowly to 100 ml of ice cold methanol. This mixture was added to a slurry of 5.39 g (9.1 mmol) of N,N',N'',N'''-tetrakis(1-hydrogen-itaconyl)-triethylenetetramine. The resulting yellow suspension was brought to reflux and stirred for four hours, during which the reaction mixture became clear. Evaporation of the volatiles yielded 4.30 g (73%) of N,N',N'',N'''-tetrakis (1-hydrogen-itaconyl)-triethylene-tetraamine, as identified by IR and $^1$H NMR. molecular weight=659.68 g/mol; 6.15 meq/g C=C.

Example 6

Synthesis of Trimethylolpropane tris[poly(propyleneglycol), itaconamide terminated]ether (36)

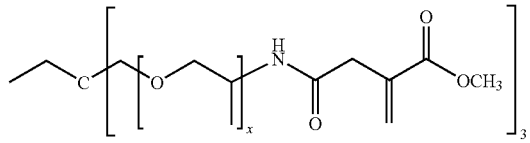

10.2 g (53.1 mmol) of N-(3-dimethylaminopropyl)-N'-ethylcarbodiimide hydrochloride and 0.40 g (3.3 mmol) of 4-(dimethylamino)-pyridine were suspended in 50 ml of dry dichloromethane under an Ar atmosphere. The suspension was cooled in an ice bath to 2° C. and 6.09 g of trimethylolpropane tris[poly(propyleneglycol), amine terminated]ether dissolved in 50 ml of dry dichloromethane were added, yielding a clear and colorless solution. 7.15 g (49.6 mmol) of 4-hydrogen-1-methyl itaconate dissolved in 40 ml of dry dichloromethane were added dropwise at such a rate that the temperature remains below 4° C. After complete addition the clear, light yellow reaction mixture was stirred for another hour at 2-3° C. and was then allowed to warm up to room temperature and stirred for one more hour. The solution was transferred to a separation funnel and washed with 50 ml of saturated aqueous NaHCO$_3$ solution, 50 ml of 1 M aqueous KHSO$_4$ solution, and 50 ml of saturated aqueous NaHCO$_3$ solution with 50 ml of saturated aqueous NaCl solution. Drying the organic layer with Na$_2$SO$_4$ and evaporation of the solvent yielded 12.8 g of the product as a clear, reddish brown oil, the structure of which is confirmed by IR, $^1$H NMR, and $^{13}$C NMR spectroscopy.

Example 7

Synthesis of Pentaerythritol tetrakis(3-mercaptopropyl)ether (27)

Step 1: Pentaerythritol tetraallylether

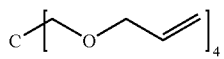

30.7 g (0.12 mol) of pentaerythritol triallylether was dissolved in 100 ml of dry THF and 4.4 g (0.18 mol) of NaH was added in small portions while stirring. After gas evolution had ceased, 16 ml (0.18 mol) of allyl bromide was added and the reaction mixture was stirred overnight at room temperature. In order to drive the reaction to completion, it was subsequently brought to reflux and stirred for 1 hr. The precipitated salts were removed by filtration over ca. 1 cm of Celite 545 and the solvent and excess allyl bromide were evaporated, yielding 35.3 g (99.5%) of a pale yellow oil. The raw product was dissolved in 100 ml of diethyl ether and washed subsequently with 50 ml of 0.1 M aqueous KHSO$_4$ and 50 ml of saturated aqueous NaHCO₃ solution. Drying the organic layer with MgSO₄ and evaporation of the solvent yielded 34.4 g (97%) of the pure product.

Step: 2 Pentaerythritol tetrakis(3-thioacetopropyl)ether

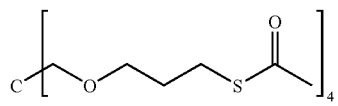

24.8 g (83.8 mmol) of pentaerythritol tetraallylether, 28.8 g (0.378 mol) of thioacetic acid, and 1.08 g (6.6 mmol) of AIBN were dissolved in 100 ml of THF, cooled to 2° C. and degassed by 3 cycles of evacuation and purging with Ar. The solution was brought to reflux and stirred for 17 hrs. Then, another 6.12 g (80.4 mmol) of thioacetic acid, and 0.51 g (3.1 mmol) of AIBN were added and the reaction mixture was stirred under reflux for another 22 hrs., after which the solvent was evaporated. Yield: 55.5 g (110%) of a yellow oil. According to ¹H NMR analysis, 98.4% of the allyl groups had been converted.

Step: 3 Pentaerythritol tetrakis(3-mercaptopropyl)ether (27)

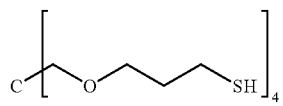

7.02 g (0.011 mol) of pentaerythritol tetrakis(3-thioacetopropyl)ether was dissolved in 30 ml of ethanol. The solution was degassed by 3 cycles of evacuation and purging with Ar and heated in a 60° C. oil bath. 30.3 g (0.27 mol) of a 50% aqueous KOH solution was added dropwise in ca. 30 min. After another 30 min. stirring the reaction mixture was allowed to cool down, poured into 100 ml of degassed 1 M aqueous KHSO₄ solution and brought to pH 2 by adding saturated aqueous KHSO₄ solution. The product was recovered by extraction with three 80 ml portions of diethyl ether. The combined organic layers were washed subsequently with 100 ml of saturated aqueous NaHCO₃ solution and 100 ml of saturated aqueous NaCl solution and dried over Na₂SO₄. Evaporating the solvent yielded 4.1 g (89%) of an amber colored oil. IR analysis showed the complete disappearance of the carbonyl signal at 1687 cm⁻¹.

Example 8

Synthesis of 1,1,1-Trimethylolpropane tris(3-mercaptopropyl)ether

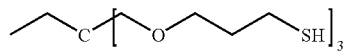

The first synthesis reaction was similar to the three steps in Example 7, however starting from 1,1,1-trimethylolpropane diallyl ether in step 1, which yielded in 1,1,1-trimethylolpropane tris(3-mercaptopropyl)ether.

A second synthesis procedure, was started from 1,1,1-trimethylol-propanol in step 1 of Example 7. The other steps were performed similarly:

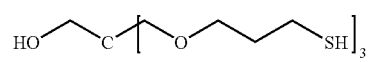

Example 9

Synthesis of 1,2,4-Tris(2-mercaptoethyl)cyclohexane

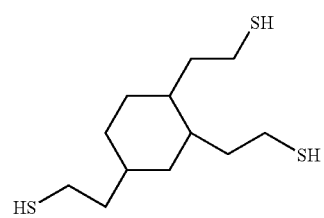

22.2 g (0.137 mol) of 1,2,4-trivinylcyclohexane, 37.2 g (0.49 mol) of thioacetic acid, and 1.4 g (8.5 mmol) of AIBN were dissolved in 140 ml of THF under an Ar atmosphere. The solution was brought to reflux and stirred for 18 hrs. After cooling down, the solution was stirred for 30 min. with Dowex WGR2 resin, in order to bind the excess of thioacetic acid and filtered. The solvent was removed by rotary evaporation and the product was dispersed in a solution of 79.3 g (1.98 mol) of NaOH in 170 ml of water under an Ar atmosphere. The dispersion was heated to 80° C. and stirred at that temperature for 4 hrs. After cooling to room temperature, concentrated hydrochloric acid was added slowly until the pH is 1 and the product was extracted with three 150 ml portions of dichloromethane. The combined organic layers were washed with 150 ml of 5% aqueous NaHCO₃ solution and with 100 ml of water and dried with MgSO₄. Removing the solvent yielded 27.3 g (76%) of the desired product.

Example 10

Synthesis of 2,4,6,8-Tetra(2-mercaptoethyl)-2,4,6,8-tetramethylcyclotetrasiloxane (21)

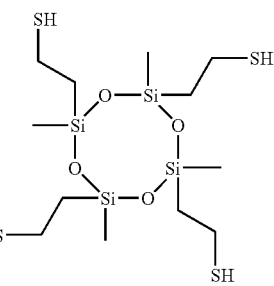

23.7 g (0.069 mmol) of 2,4,6,8-Tetravinyl-2,4,6,8-tetramethylcyclotetrasiloxane, 25.2 g (0.331 mmol) of thioacetic acid, and 0.91 g (5.5 mmol) of AIBN were dissolved in 110 ml of THF and flushed with nitrogen. The reaction mixture was heated to reflux for 15 hrs., after which it was cooled down to 40° C. and the THF was distilled off at reduced pressure. The resulting oil was dissolved in 100 ml of ethanol and at room temperature 29 ml of 50% aqueous NaOH were added, causing the temperature to rise to 48° C. After the addition was complete, the mixture was heated to reflux for 4 hrs. and the mixture was concentrated to 25% of its original volume at reduced pressure. After cooling to room temperature, 187 g of 30% $H_2SO_4$ in water were added slowly. The product was extracted from the mixture with three 100 ml portions of dichloromethane. The combined organic layers were washed twice with 180 ml of saturated aqueous $NaHCO_3$ solution. Evaporating the solvent and drying on the rotavap at 10 mbar for 5 hrs. yielded 32.9 g (99%) of a viscous, yellow oil. Molecular weight=480.99 g/mol; 8.82 meq/g SH.

Example 11

Synthesis of Tetra(3-mercaptopropyl)silane

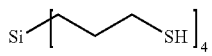

The above procedure (Example 10) was used, but starting from tetraallyl silane. Tetra(3-mercaptopropyl)silane was synthesized, with a 94% yield.

Example 12

Synthesis of tri(3-mercaptopropyl)trimethylolpropane (25)

Step 1: Trimethylolpropane Triallylether 48 ml (0.224 mol) of trimethylolpropane diallyl ether was slowly added to 120 ml THF and 6.5 g (0.271 mol) of NaH in a 500 ml round bottom flask, Slow development of bubbles indicated the start of the redox reaction between R—OH and Na. The solution was stirred overnight. 23 ml (0.032 mol) of allyl bromide was dropped to the solution. Mixture got warm and milky and the suspension was left overnight. The solution was transferred into a separation funnel and the product was washed with $H_2O$, $KHSO_4$, again $H_2O$ and NaCl. The organic layer was dried with $MgSO_4$ and evaporated.

Step 2: Radical Addition of Thiacetic Acid to Allylic Groups 41 g (0.164 mol) of trimethylolpropane triallylether, 36.7 ml (0.59 ml) of thioacetic acid and 1.67 g of AIBN were dissolved in 150 ml of THF in a 500 ml round bottom flask, equipped with reflux condenser, thermometer and magnetic stirrer bar. The solution was stirred at 65° C. for 18 h. To bind thiacetic acid, 37 g of Dowex WGR-2 was added. After 30-40 min of stirring, the solution was filtrated and dried with $MgSO_4$.

Step 3: tri(3-mercaptopropyl)trimethylolpropane 96 g (2.4 mol) of NaOH and thioacetyl ester were added in 200 ml of water, stirring at 80° C. for 4 h. By addition of 200 ml of HCl, the suspension was acidiphicated. 200 ml of chloroform was added and after 30 min transferred to a separation funnel. The solution was washed four times with water and 2 times with brine. The organic layer was dried with $MgSO_4$ and the solvent was removed by rotary evaporation, yielding 38.1 g Example 13

Synthesis of Polypropylenoxid-α,ω-bis(1-propyl-itaconylamide) (45)

Step 1: Polypropylenoxid-α,ω-bis(1-propyl-itaconylamide) free acid 15.5 g (0.138 mol) itaconic anhydride was dissolved in 100 ml $CH_2Cl_2$. The solution was filtered to remove traces of insoluble itaconic acid and was slowly added to 75 ml (0.0375 mol) of Jeffamine D-2000 in 400 ml borate buffer (0.1 M, 9.5 pH with NaOH) in a 1 l round bottom flask, equipped with reflux condenser, thermometer, magnetic stirrer bar and dropping funnel. The pH was kept at 9.5 by addition of NaOH. After stirring the reaction mixture overnight, 200 ml of water was added and the resulting suspension was transferred to a separation funnel and the product was extracted by washing five times with 250 ml of diethyl ether and by washing two times with 200 ml of brine. The organic layer was dried over $MgSO_4$ and the solvent was removed by rotary evaporation, yielding 63.1 g (76%) of product.

Step 2: Polypropylenoxid-α,ω-bis(1-propyl-itaconylamide) (36)

8.2 ml (0.112 mol) of thionyl chloride was slowly added to 100 ml of icecooled 1-propanol from a dropping funnel. 62 g (0.028 mol) of PPOdiItAm free acid, dissolved in 200 ml of primary alcohol, was added. Then the solution was brought to a light reflux and was stirred for 4 h. The solution was concentrated by rotary evaporation and 100 ml of chloroform was added. The solution was transferred to a separation funnel and the product was washed twice with 150 ml of saturated aqueous $NaHCO_3$ solution and twice with 150 ml of brine. The organic layer was dried with $MgSO_4$ and the solvent was removed by rotary evaporation, yielding 49.8 g (81%) of the derived product.

Example 14

Polypropylenoxid-α,ω-bis(1-propyl-acrylamideamide) (46)

100 ml (0.049 mol) of Jeffamine D-2000 and 11.4 g (0.107 mol) of $Na_2CO_3$ were added to 200 ml chloroform in a 500 ml round bottom flask, equipped with reflux condenser, magnetic stirrer, thermometer and dropping funnel. 8.7 ml (0.107 mol) of acryloyl chloride, dissolved in 20 ml chloroform was added slowly to the solution and stirred for 2 days. The solution was filtrated and transferred to a separation funnel and the product was washed twice with concentrated aqueous $NaHCO_3$ solution and twice with brine. The organic layer was dried with $MgSO_4$, and the solvent was removed by rotary evaporation, yielding 72.3 g (68%) of slightly yellow oil.

Examples 15-26

Formation of Compositions for Use in Vertebroplasty

The silica used in Examples 15-26 is commercially available from Cabot GmbH under the tradename CAB-O-SIL M-5; it is hydrophil with an average particle size of 12 nm.

100 μm BaSO$_4$ is commercially available from Riedl-de Haelme (No. 11432 in Sigma Aldrich catalogue) or from Sachtleben Chemie GmbH under the trade name Sachtoperse HP, HU-N. Trimethylolpropane triacrylate is commercially available in purities above 95% from Sartomer Mixing of the dispersions/mixtures (both terms are used synonymously herein) was performed by a Ultra-Turrax T25 basic equipped with S25N-10G dispersion stick. Mixing took place at level 6 until homogeneity was achieved.

As used herein, the term "component" includes the reactive species and any additive added beforehand. For example, "thiol component" or "itaconate component" indicates the respective species of thiol or itaconate itself plus fillers, X-ray agents, bases such as SiO$_2$ or BaSO$_4$ or triethylamine.

As used herein, weight % indicates weight percentages of the total weight of the composition.

Example 15

Formation of Composition from trimethylolpropane triacrylate and 2,3,6,8-Tetra(2-mercaptoethyl)-2,4,6,8-tetramethylcyclotetrasiloxane Formation of Bulk Material 2 g of BaSO$_4$ and 0.74 g of SiO$_2$ were dispersed in 20 g of trimethylolpropane triacrylate (30) until homogeneity ("acrylate component"). 2 g of BaSO$_4$ and 0.74 g of SiO$_2$ were dispersed in 20 g of 2,3,6,8-Tetra(2-mercaptoethyl)-2,4,6,8-tetramethylcyclotetrasiloxane (21) and mixed until homogeneity ("thiol component").

150 mg tributylamine was added to 1.16 g of the "acrylate component" and mixed until homogeneity to form the "acrylate/tributylamine component". Subsequently, 1.5 g of the "thiol component" was mixed with the "acrylate/tributylamine component" until homogeneity was achieved.

Characteristics of Resulting Biomaterial

Weight % SiO$_2$: 3.1; Weight % BaSO$_4$: 8.38
Gelation time: about 10 minutes at 37° C.; Stability: ☐1 year at 37° C.;
Ultimate compressive strength 27 MPa;
Young's modulus E: 110 MPa at 10% strain and 0.35 mm/s;
Water uptake 0.2%.

Example 16

Formation of Composition from 2,3,6,8-Tetra(2-mercaptoethyl)-2,4,6,8-tetramethylcyclotetrasiloxane and trimethylolpropane tris[poly(propyleneglycol), amine terminated]ether ("TPGA")

Formation of Bulk Material 300 mg of SiO$_2$ and 2000 mg of BaSO$_4$ were dispersed in 6000 mg (49.86 mmol —SH) of 2,3,6,8-Tetra(2-mercaptoethyl)-2,4,6,8-tetramethylcyclotetrasiloxane (21) ("thiol component"). Then 637.3 mg (3.99 mol —NH$_2$) of trimethylolpropane tris[poly(propyleneglycol), amine terminated]ether ("TPGA") was added to the thiol component and mixed thoroughly ("thiol component"/TPGA mixture).

110 mg of SiO$_2$ and 1406 mg of BaSO$_4$ were dispersed in 8531 mg (49.86 mmol C=C) of 1,1,1-tris(hydroxymethyl) propane-tris(1-methyl itaconate) ("itaconate component") (35).

Subsequently the "thiol component"/TPGA mixture and the "itaconate component" were combined and mixed until homogeneity was achieved.

Characteristics of Resulting Biomaterial

Weight % SiO$_2$: 2.16; Weight % BaSO$_4$: 17.94; Weight % of sum of donor and acceptor: 76.55; weight % base: 3.36.
Gelation time: about 13 minutes at 37° C.; Stability: ≧1 year at 37° C.;
Young's modulus E 35 MPa at 10% strain and 0.35 mm/s;
Water uptake 1.8%;
Viscosity up to 400 s 3 Pa/s.

Example 17

Formation of Composition from trimethylolpropane triacrylate and 2,3,6,8-Tetra(2-mercaptoethyl)-2,4,6,8-tetramethylcyclotetrasiloxane Formation of Bulk Material 2800 mg (26.11 mmol —C=C—) of commercially available trimethylolpropane triacrylate (30) was mixed homogenously with 100 mg of (1.06 mmol —NH$_2$) triethylamine ("acrylate component"). Then, 3200 mg (26.11 mmol —SH) of 2,3,6,8-Tetra(2-mercaptoethyl)-2,4,6,8-tetramethylcyclotetrasiloxane (21) (thiol components) was added to the "acrylate component" and the dispersion was mixed until homogeneity was reached.

Characteristics of Resulting Biomaterial

Gelation time: about 10 min at 37° C.;
Stability: ≧1 year at 37° C.; Young's modulus E: 60 MPa at 10% strain and 0.35 ml/s; Water uptake 2%.

Example 18

Formation of Composition from 1,1,1-tris(hydroxymethyl)propane-tris(1-methyl itaconate) and 2,3,6,8-Tetra(2-mercaptoethyl)-2,4,6,8-tetramethyl-cyclotetrasiloxane Formation of Bulk Material 800 mg of (6.653 mmol —C=C—) 1,1,1-tris(hydroxymethyl)propane-tris(1-methyl itaconate) (35) was mixed homogenously with 33 mg (0.33 mmol-NH$_2$) of triethylamine ("itaconate component").

Subsequently, 1000 mg (8.316 mmol —SH) of 2,3,6,8-Tetra(2-mercaptoethyl)-2,4,6,8-tetramethylcyclotetrasiloxane (21) was added to the "itaconate component" and mixing was continued until homogeneity was achieved.

Characteristics of Resulting Biomaterial

Gelation time: about 15 min at 37° C.;
Stability: ≧1 year at 37° C.; Young's modulus E: 15 MPa at 10% strain and 0.35 mm/s; Water uptake 2.3%.

Example 19

Formation of Composition from 1,1,1-tris(hydroxymethyl)propane-tris(1-methyl itaconate) and 2,3,6,8-Tetra(2-mercaptoethyl)-2,4,6,8-tetramethyl-cyclo-tetrasiloxane Formation of Bulk Material 3570 mg (23.56 mmol —C=C—) of 1,1,1-tris(hydroxymethyl)propane-tris(1-methyl itaconate) (35) was mixed homogenously with 92 mg (0.94 mmol —NH$_2$) of triethylamine ("itaconate component"). 2829 mg (23.56 mmol —SH) of 2,3,6,8-Tetra(2-mercaptoethyl)-2,4,6,8-tetramethylcyclo-tetrasiloxane (21) was added to the "itaconate component" and mixing was continued until homogeneity was reached.

Characteristics of Resulting Biomaterial
Gelation time: about 14 min at 37° C.; Stability: ≧1 year at 37° C.; Young's modulus E: 25 MPa at 10% strain and 0.35 mm/s; Water uptake 2.4%.

Example 20

Formation of composition from tetrakis(1-methyl-itaconyl)-triethylenetetramine and 2,3,6,8-Tetra(2-mercaptoethyl)-2,4,6,8-tetramethylcyclo-tetrasiloxane Formation of Bulk Material
21 mg (0.21 mmol —$NH_2$) of triethylamine were added to and mixed with 567 mg (3.94 mmol —C═C—) of tetrakis (1-methyl-itaconyl)-triethylenetetramine (34) ("itaconamide components"). 420 mg (3.94 mmol —SH) 2,3,6,8-Tetra(2-mercaptoethyl)-2,4,6,8-tetramethylcyclo-tetrasiloxane (21) was added to the "itaconamide component" and mixing was continued until homogeneity was reached.
Characteristics of Resulting Biomaterial
Stability: ≧1 year at 37° C.; Young's modulus E: around 200 MPa at 10% strain and 0.35 mm/s.

Example 21

Formation of composition from Triglycerol-penta(1-methyl itaconate) and 2,3,6,8-Tetra(2-mercaptoethyl)-2,4,6,8-tetramethylcyclotetrasiloxane Formation of Bulk Material
434.5 mg (2.945 mmol —C═C—) of Triglycerol-penta(1-methyl itaconate) (31) was mixed with 12.6 mg (0.124 mmol) of triethylamine ("itaconate component"). 300 mg (2.945 mmol —SH) 2,3,6,8-Tetra(2-mercaptoethyl)-2,4,6,8-tetramethylcyclotetrasiloxane (21) was added to the "itaconate component" and mixed until homogeneity was achieved.
Characteristics of Resulting Biomaterial
Gelation time: about 30 min at 37° C. Young's modulus E: 30 MPa at 10% strain and 0.35 mm/s. Stability: ≧1 year at 37° C.

Example 22

Formation of Composition from 2,3,6,8-Tetra(2-mercaptoethyl)-2,4,6,8-tetramethylcyclotetrasiloxane/TGPA and 1,1,1-tris(hydroxymethyl)propane-tris(1-n-butyl itaconate)

Formation of Bulk Material
34 mg of $SiO_2$ and 289 mg of $BaSO_4$ were dispersed homogenously in 1200 mg (11.09 mmol —SH) of 2,3,6,8-Tetra(2-mercaptoethyl)-2,4,6,8-tetramethylcyclotetrasiloxane (21). Then 84 mg (0.83 mmol —$NH_2$) of trimethylolpropane tris[poly(propylenglycol), amine terminated]ether (TPGA) was added to the latter and the dispersion was mixed thoroughly ("thiol component").
63 mg of $SiO_2$ and 531 mg of $BaSO_4$ were dispersed homogenously in 2360 mg (11.09 mmol —C═C—) of 1,1,1-tris(hydroxymethyl)propane-tris(1-n-butyl itaconate) (32) ("itaconate component"). The "thiol component" and the "itaconate component" were combined and mixing of the combined mixture was continued until homogeneity was reached.
Characteristics of Resulting Biomaterial
Weight % $SiO_2$: 2.13; Weight % $BaSO_4$: 17.98; Weight % of sum of donor and acceptor: 78.05; weight % base: 1.84.
Gelation time: 13 min at 37° C.; Stability≧1 year at 37° C.; Young's modulus B:
MPa at 10% strain and 0.35 mm/s; Water-uptake 2.0%.

Example 23

Formation of Composition from 2,3,6,8-Tetra(2-mercaptoethyl)-2,4,6,8-tetramethylcyclotetrasiloxane/TPGA and Trimethylolpropane tris[poly(propyleneglycol), itaconamide terminated]

Formation of Bulk Material
20 mg of $SiO_2$ and 169 mg of $BaSO_4$ were dispersed homogenously in 700 mg (6.47 mmol —SH) of 2,3,6,8-Tetra (2-mercaptoethyl)-2,4,6,8-tetramethylcyclotetrasiloxane (21). In a next step 49 mg (0.49 mmol —$NH_2$) of trimethylolpropane tris[poly(propylenglycol), amine terminated] ether (TPGA) was added to the dispersion which was then mixed thoroughly. ("thiol component").
48 mg of $SiO_2$ and 398 mg of $BaSO_4$ were homogenously dispersed in 1767 mg (6.47 mmol —C═C—) of Trimethylolpropane tris[poly(propyleneglycol), itaconamide terminated] (36) ("itaconamide-component"). In the next step, the "thiol component" and the "itaconamide-component" were combined and mixing of the combined mixture was continued until homogeneity was reached.
Characteristics of Resulting Biomaterial
Weight % $SiO_2$: 2.16; Weight % $BaSO_4$: 17.99; Weight % of sum of donor and acceptor: 78.3; weight % base: 1.56.
Gelation time: 13 min at 37° C.; Stability: ≧1 year at 37° C.; Young's modulus E: 25 MPa at 10% strain and 0.35 mm/s; Water uptake 5%.

Example 24

Formation of Composition from pentaerithritol tetrakis(2-mercaptoprionate) and trimethylolpropane triacrylate Formation of Bulk Material
0.406 g of $SiO_2$ and 3.456 mg of $BaSO_4$ were homogenously dispersed in 15 g (119.62 mmol —SH) of pentaerithritol tetrakis(2-mercaptoprionate) (26) ("thiol component").
0.387 g of silica and 2.9 g of $BaSO_4$ were dispersed in 12.91 g (119.62 mmol C═C) of trimethylolpropane triacrylate (30). Then 0.362 g (3.58 mmol $NH_2$) of triethylamine was added and mixed thoroughly ("acrylate component"). The acrylate component and the thiol component were combined and the combined mixture was mixed until homogeneity was reached.
Characteristics of Resulting Biomaterial
Weight % $SiO_2$: 2.24; Weight % $BaSO_4$: 17.94; Weight % of sum of donor and acceptor; 78.8; weight % base: 1.02.
Young's modulus E 43 MPa at 10% strain and 0.35 mm/s;
Young's modulus E, uniaxial compressive strength and Poisson's ratio at 0.3% strain and 0.005 mm/s: Young's modulus E 33.3 MPa, Poisson's ratio: 0.47; uniaxial compressive strength of 11.3 MPa.

Example 25

Formation of Composition from 2,3,6,8-Tetra(2-mercaptoethyl)-2,4,6,8-tetramethylcyclotetrasiloxane/TPGA and 1,1,1-tris(hydroxymethyl) propane-tris(1-methyl itaconate)

Formation of Bulk Material
117 mg of $SiO_2$ and 978 mg of $BaSO_4$ were dispersed homogenously in 4000 mg (28.27 mmol —SH) of 2,3,6,8-

Tetra(2-mercaptoethyl)-2,4,6,8-tetramethylcyclotetrasiloxane (21). Subsequently 349 mg (2.2 mmol —$NH_2$) trimethylolpropane tris[poly(propylenglycol), amine terminated] ether (TPGA) was added to the dispersion which was mixed thoroughly ("thiol component"). 115 mg of $SiO_2$ and 965 mg of $BaSO_4$ were dispersed homogenously in 4289 mg of (22.62 mmol —C═C—) of 1,1,1-tris(hydroxymethyl)propane-tris(1-methyl itaconate) (35) ("itaconate component).

The "thiol component" were added to the "itaconate component" and mixing of the combined mixture was continued until homogeneity was achieved. Ratio 1,1,1-tris(hydroxymethyl)propane-tris(1-methyl itaconate) (35) to 2,3,6,8-Tetra(2-mercaptoethyl)-2,4,6,8-tetramethylcyclotetrasiloxane (21)=0.8.

Characteristics of Resulting Biomaterial

Weight % $SiO_2$: 2.15; Weight % $BaSO_4$: 17.97; Weight % of sum of donor and acceptor: 76.66; weight % base: 3.23.

Gelation time: 15 min at 37° C.; Young's modulus E: 30 MPa at 10% strain and 0.35 mm/s; Stability≧1 year at 37° C.

Example 26

Formation of Composition from 2,3,6,8-Tetra(2-mercaptoethyl)-2,4,6,8-tetramethylcyclotetrasiloxane/TPGA and 1,1,1-tris(hydroxymethyl)propane-tris(1-methyl itaconate)

Formation of Bulk Material 187 mg of $SiO_2$ and 978 mg of $BaSO_4$ were dispersed homogenously in 4000 mg (28.27 mmol —SH) of 2,3,6,8-Tetra(2-mercaptoethyl)-2,4,6,8-tetramethylcyclotetrasiloxane (21). Subsequently, 349 mg (2.2 mmol —$NH_2$) trimethylolpropane tris[poly(propylenglycol), amine terminated] ether (TPGA) was added to the latter and the dispersion was mixed thoroughly ("thiol component").

184 mg of $SiO_2$ and 965 mg of $BaSO_4$ were dispersed homogenously in 4289 mg (22.62 mmol —C═—) of 1,1,1-tris(hydroxymethyl)propane-tris(1-methyl itaconate) (35) ("itaconate component). The "itaconate component" and "thiol component" were combined and mixing of the combined mixture was continued until homogeneity was achieved.

Ratio 1,1,1-tris(hydroxymethyl)propane-tris(1-methyl itaconate) (35) to 2,3,6,8-Tetra(2-mercaptoethyl)-2,4,6,8-tetramethylcyclotetrasiloxane (21) 0.8.

Characteristics of Resulting Biomaterial

Weight % $SiO_2$: 3.39; Weight % $BaSO_4$: 17.74; Weight % of sum of donor and acceptor: 75.68; weight % base: 3.19.

Gelation time: 15 min at 37° C.; Young's modulus E: 37 MPa at 10% strain and 0.35 mm/s; Stability≧1 year at 37° C.

Example 27

Synthesis of tetra(3-mercaptopropyl)silane (29)

Step 1: 200 g of Tetraallylsilane is reacted with 792 g of thioacetic acid in 1600 mL THF using 8.54 g of azobisisobutyronitrile (AIBN) as a free radical source. The reaction is carried out at 65° C. After reaction completion a part (approximately 2/5) of the THF is removed by distillation and ethyl acetate is added to the reaction mixture. The mixture is washed with water, hydrogen carbonate (aq) and brine. After concentration and co-evaporation with toluene 535 g of the crude tetrakis-(thioacetylpropyl)-silane is obtained as an oil (yield 104%).

Step 2: 579 g of crude tetrakis-(thioacetylpropyl)-silane is mixed with 1500 mL Methanol, cooled to 0° C. and 180 g of an aqueous solution of NaOH slowly added to affect hydrolysis of the acetyl moiety. After reaction completion the reaction mixture is neutralized with HCl (aq) and extracted with toluene. After washings (water), drying (N2SO4) and concentration 303 g of the crude tetra(3-mercaptopropyl)silane (29) is obtained as an oil (yield 78%). The crude tetra(3-mercaptopropyl)silane (29) is purified using flash chromatography on silica gel with toluene/heptane (1:1) as eluent.

Example 28

Formation of Composition from Tetra(3-Mercaptopropyl)Silane and Dipentaerythritol Penta-Acrylate Formation of Bulk Material 5.44 g of tetra(3-mercaptopropyl)silane (29) (24.5% w/w) and 4 g of dipentaerythritol penta-acrylate (43) (CAS registry number 60506-81-2, obtained from polysciences inc.) (17.6% w/w) were mixed together with a stainless-steel spatula for about 1 minute until homogeneity was achieved. 0.225 g of tributylamine (1% w/w) was added to the mixture of acceptor and donor. The mixture of acceptor, donor and base was further homogenized with the aid of the stainless-steel spatula. The adding of the base was taken as the "time-zero" reference point for the start of the polymerization reaction. 12.5 g of barium sulfate (56.4% w/w) was then poured into the liquid mixture of acceptor, donor and base. The mixture was manually homogenized for about 2 minutes with the aid of the stainless-steel spatula, and then transferred to vertebroplasty gun barrel (OptiMed Cemento-RE gun). The material was used within 15 minuters from the addition of the base.

Characteristics of Resulting Biomaterial

Figure 3A:
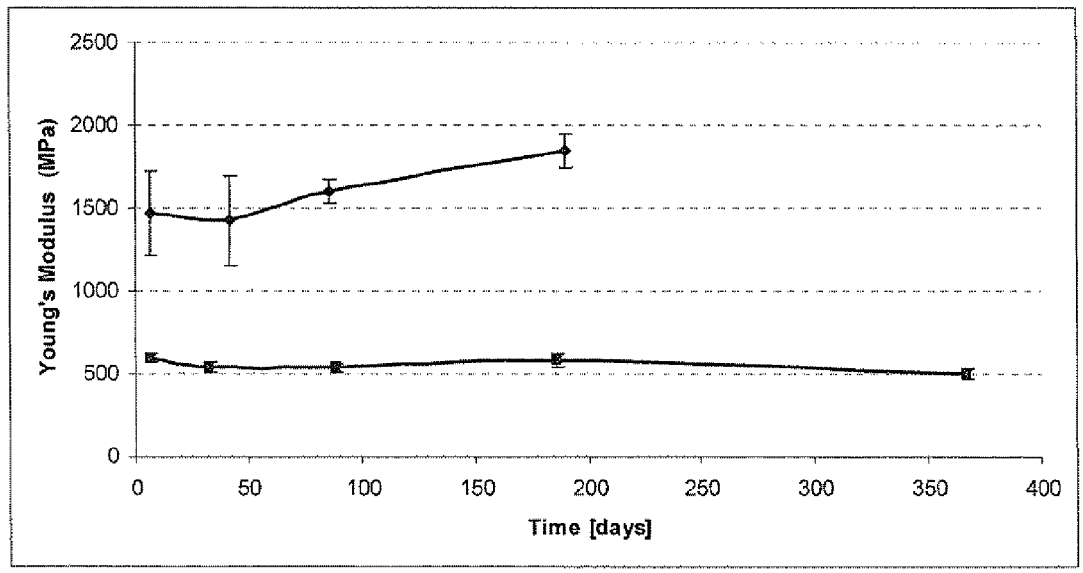
FIG. 3A is a comparison of Young's modulus (MPa) versus time (days) between a PMMA cement (♦) (KyphX HV-R cement, Medtronic) measured at 3% strain and 0.04 mm/s and a biomaterial (■) formed by reacting tetra(3-mercaptopropyl)silane and dipentaerythritol penta-acrylate in the presence of barium sulfate (BaSO4).
Figure 3B:
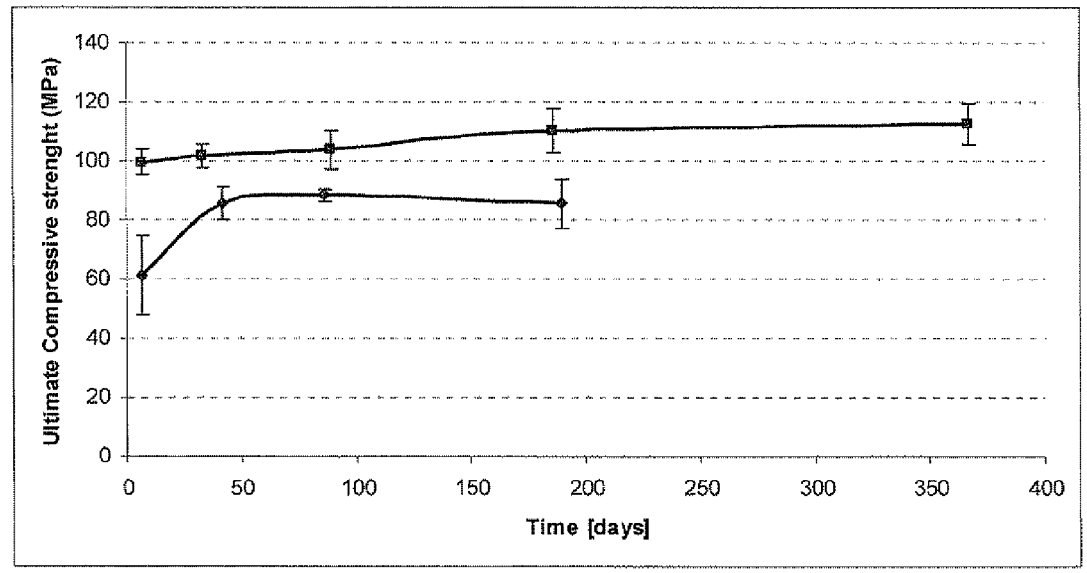
FIG. 3B is a comparison of ultimate compressive strength (MPa) versus time (days) between a PMMA cement (♦) (KyphX HV-R cement, Medtronic) and a biomaterial (■) formed by reacting tetra(3-mercaptopropyl)silane, and dipentaerythritol penta-acrylate in the presence of barium sulfate (BaSO4).

Gelation time: about 25 minutes at 23° C.; Stability: ☐1 year at 37° C.;

Ultimate compressive strength is between 100 and 10 MPa (FIG. 3b);

Young's modulus E is between 60 and 80 MPa at 10% strain and 0.35 mm/s (between 500 and 600 MPa at 3% strain and 0.04 mm/s (FIG. 3a));

Water uptake after 1 year in PBS solution at 37° C.: 2.5%.

Example 29

Testing of Augmentation Effect on Vertebrae Using Composition of Example 24

The technique consists of injecting a biomaterial percutaneously into the diseased vertebra to augment its mechanical properties. Vertebroplasty was reported to provide the patient a rapid relief from pain that is most probably due to the immediate mechanical stabilization of existing microfractures. The most commonly used biomaterial for this application is PMMA. PMMA stiffness is significantly higher than the stiffness of healthy vertebral trabecular bone. Injection of PMMA alters therefore the load distribution across the endplate and has been shown to increase the incidence of fractures in adjacent vertebrae. In addition, the consequences of bone remodeling associated with this new load distribution remain unknown.

The objective of this study was to quantify the augmentation of the mechanical properties of vertebral cancellous bone using a compliant biomaterial. An osteoporotic vertebra of a dead human body was injected and the vertebra was filled completely with composition of Example 24.

Materials and Methods

Fresh vertebral bodies were obtained post-mortem from 5 donors and stored at −26° C. After isolation from soft tissues, the vertebral bodies were fixed with cement and a pair of cylindrical cores of 8 mm diameter were extracted from each vertebra with a diamond-coated coring tool. The ends of the cylinders were cut planoparallel with a diamond-coated band saw to provide a length of 10 mm. The marrow of the samples was then removed using 3 successive baths in a smooth soap solution followed by rinsing under water and ultrasound shaking. A preliminary study verified that the morphological and mechanical properties of the cancellous bone specimens were not altered by this procedure (n=15, p>0.63). All specimens were imaged in a μCT system (μCT 40, Scanco Medical, Switzerland) at 20 μm resolution and the datasets subjected to 3D morphological analysis. A mold was designed and built in order to inject a biomaterial into the trabecular structure of the cored and marrow extracted specimens which minimized the presence of air bubbles. For gripping, both extremities of the specimen were embedded into PMMA cylinders of 12 mm length. One specimen of each pair was randomly assigned to be augmented.

Figure 1B:
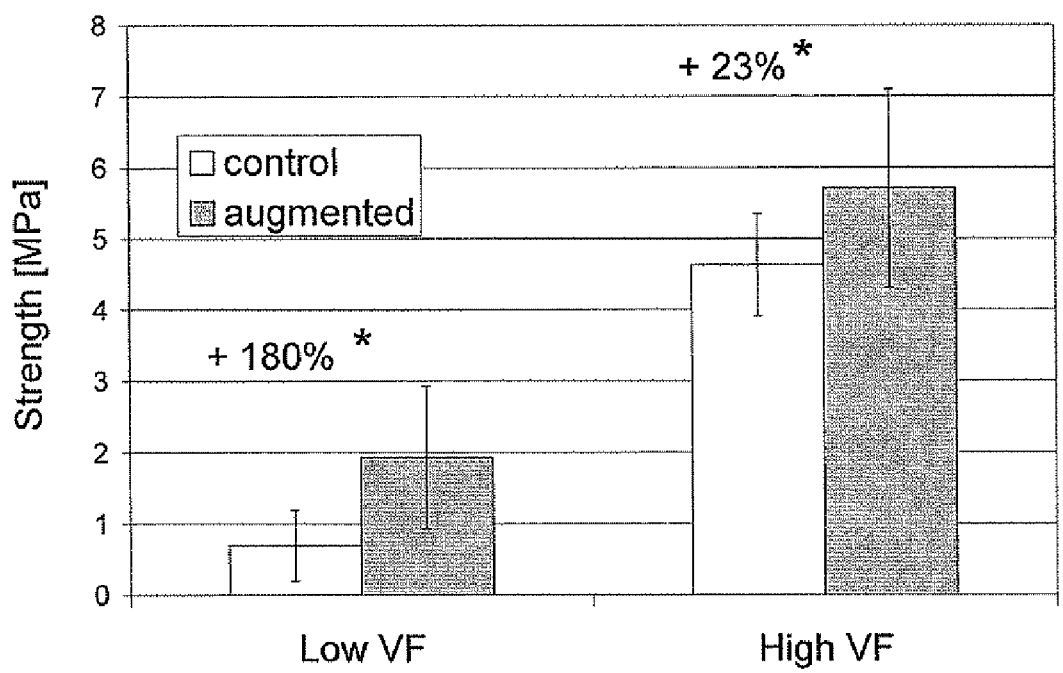
FIG. 1B shows a comparison of strength (MPa) between a control and an augmented group of vertebrae for both low and high volume fractions (VF) p<0.05).

Elastic modulus, ultimate stress (strength), ultimate strain and total energy at ultimate stress were calculated from the resulting stress-strain curves. Volume fraction and tissue density of the control specimens were obtained by Archimedes' method. Student's t-tests were applied to compare the morphological and mechanical properties between the control and augmented Results The range of bone volume fraction extended from 3.5 to 19.5%. Mean volume fraction of the control and the augmented group was not statistically different (n=24, p>0.43). The structural model index (SMI), the degree of anisotropy and the connectivity density were also comparable in the control and the augmented group (p>0.1). Since the distribution of morphological properties was bimodal, the results are presented for two separate ranges of volume fraction (VF): a low VF (n=5) and a high VF range (n=19) with a cutoff value of 10.0%. As shown in FIG. 1a, the mean elastic modulus of the augmented specimens was not significantly higher than the one of the controls for both low and high VF (p>0.13). For low VF the ultimate stress increased from 0.69±0.50 to 1.93±0.99 MPa due to augmentation (+180%), and for high VF it increased from 4.63±0.7 to 5.71±1.4 MPa (+23%). The increase in strength was found to be significant in both ranges (p<0.037). The other post yield properties, ultimate strain and total energy were also found to be higher in the augmented group (see FIG. 1b).

Discussion

Augmentation of the mechanical properties of vertebral trabecular bone by injection of a compliant biopolymer was evaluated in vitro. The use of an almost incompressible biomaterial with an Young's modulus E as low as 33 MPa was shown to enhance significantly the postyield properties and preserve elasticity of the trabecular structure. The biopolymer provides a gain in strength of approximately 1 MPa, which implies an improved relative augmentation for bone with low VF. The injection of marrow-free cylindrical specimens under laboratory conditions represents a reproducible, but best case scenario for bone augmentation. Nevertheless, the selected biopolymer may stabilize the microfractures existing in diseased vertebra and prevent the accumulation of further damage without altering significantly the stress distribution under physiological loading.

Example 30

Testing of Augmentation Effect on Vertebrae Using Composition of Example 15

An osteoporotic vertebra of a dead human body was injected and the vertebra was filled completely with composition of Example 15.

A total of 84 cylindrical specimens (Ø8 mm, L=10 mm) were cored out under constant water irrigation from cadaveric human (three male and one female) thoracic and lumbar vertebrae with age ranging from 29 to 86 years. Half of the specimens were augmented with the composition of Example 15. Since there was no previous study investigating the fatigue behavior of human trabecular bone, a protocol was adapted from one described in the literature for bovine trabecular bone (Michel M. C. et al, 1993, *Journal of Biomechanics*, 26, 453-463). During mechanical testing, the specimens were immersed in Hank's balanced salt solution at 37° C.

Results

Figure 2:
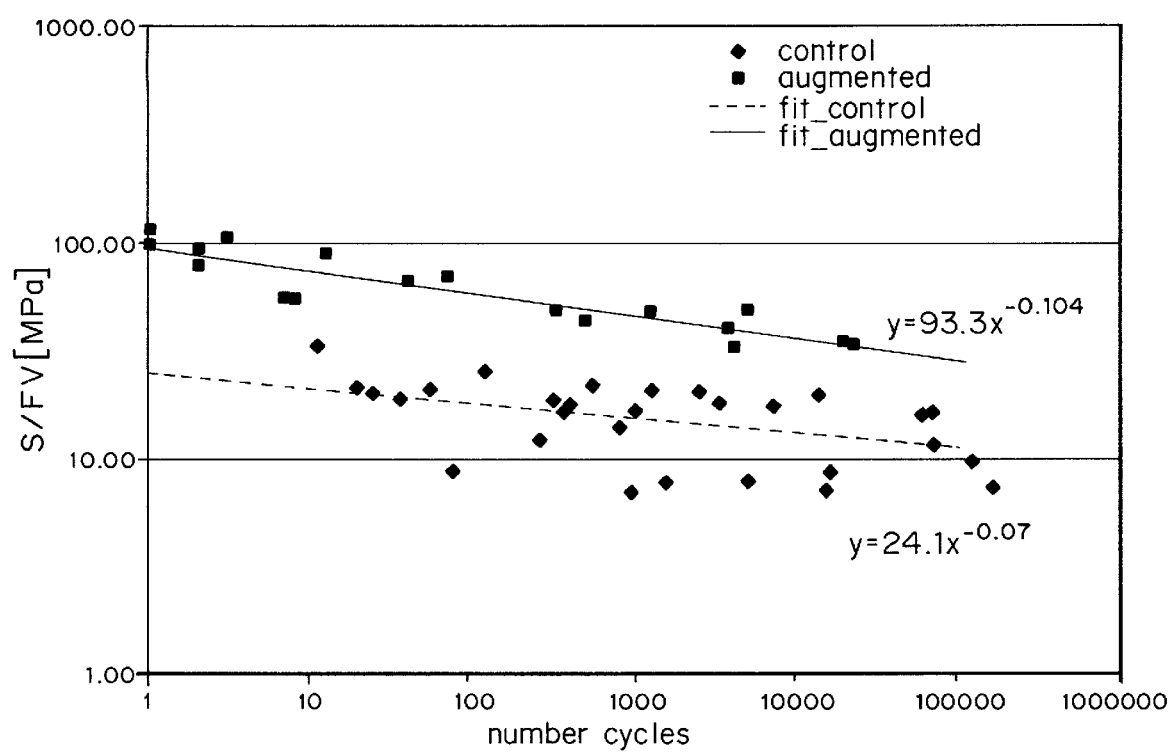
FIG. 2 is a graph showing the maximal applied stress (Smax) divided by volume fraction (FV) (MPa) versus the number of cycles to failure (N), which compares the fatigue result of augmented trabecular bone (augmented group) to non-augmented trabecular bone (control group).

The results are presented in FIG. 2, showing the maximal applied stress S max divided by volume fraction FV as a function of the number of cycles to failure Nf. Smax was divided by FV to normalize the data since Smax is strongly dependant upon FV.

A comparison between the fatigue result of the augmented trabecular bone (augmented group) to non-augmented trabecular bone (control group) shows a substantial increase in the fatigue life of trabecular bone for the augmented group (see FIG. 2).

Example 31

Testing of Compressive Strength of Composition of Example 16 when Applied to Vertebra An osteoporotic vertebra of a dead human body was injected and the vertebra was filled completely with composition of Example 16. The compressive strength of osteoporotic vertebra prior to augmentation (spongy part) was 0.7 at 0.03% strain and 0.027 mm/s. The compressive strength of vertebra (spongy part) with augmentation was 2.1 MPa at 0.03% strain and 0.027 mm/s.

Example 32

Composition for Use in Urological Bulking 0.092 g of $SiO_2$ was dispersed homogenously in 2.4 g (20.19 mmol —SH) of Tris(3-mercaptopropyl)trimethylolpropane (24). Then, 0.636 g (6.05 mol —$NH_2$) of diethanolamine is added to the thiol/$SiO_2$ dispersion and mixed thoroughly ("thiol component").

0.180 g of $SiO_2$ was dispersed homogenously in 7.067 g (20.19 mmol —C=C—) of polypopyleneoxide α-ω-bis(1-propyl itaconamide) (45) ("itaconamide component"). The "thiol component" and the "itaconamide component" were combined and mixed until homogeneity was achieved.

Characteristics of Resulting Biomaterial

Weight % $SiO_2$: 2.63; Gelation time: about 30 minutes at 37° C. At 70° C. the composition is stable for 60 days. The Young's modulus E at 0.1 strain is around 2 MPa; Water-uptake: 15%.

Example 33

Composition for Use in Urological Hulking 0.070 g of $SiO_2$ was dispersed homogenously in 2.400 g (19.14 mmol SH) of pentaerythritol tetrakis(2-mercaptopropionate) (26) ("thiol component"). 0.400 g of SiO$_2$ was dispersed homogenously in 15.074 g (33.49 mmol —C=C—) commercially available poly(propylene oxide) diacrylate (44) (Sigma). Subsequently 0.191 g (0.957 mmol —NH$_2$) of Jeffamine D-400 was added to the acrylate/SiO$_2$ dispersion and mixed thoroughly ("acrylate component"). The "thiol component" and the "acrylate component" were combined and mixing was continued until homogeneity was achieved.

Characteristics of Resulting Biomaterial

Weight % SiO$_2$: 2.59; Gelation time: about 30 minutes at 37° C. At 37° C. the composition was stable for more than 250 days; Young's modulus E at 0.1 strain: 0.2 MPa. Water-uptake: 10%.

Example 34

Composition for Use in Urological Bulking 0.030 g of SiO$_2$ was dispersed homogenously in 1.100 g (11.64 mmol —SH) of 1,2,4-Tris(2-mercaptoethyl)cyclohexane (22) ("thiol component"). 0.130 g of SiO$_2$ was dispersed homogenously in 4.891 g (13.97 mmol —C=C—) of polypropyleneeoxide α-ω-bis(1-propyl itaconamide) (45). In a next step 0.116 g (0.957 mmol —NH$_2$) of Jeffamine D-400 was added to the itaconamide/SiO$_2$ mixture and mixed thoroughly ("itaconamide component"). The "itaconamide component" and the "thiol component" were combined and mixing was continued until homogeneity was achieved.

Characteristics of Resulting Biomaterial

Weight % SiO$_2$: 2.55; Gelation time: in about 30 minutes at 37° C. Stability≧1 year at 37° C.; Young's modulus E at 0.1 strain is around 1 MPa. Water-uptake: 12%.

Example 35

Composition for Use in Urological Bulking 0.070 g of SiO$_2$ was homogenously dispersed in 2.2 g (17.27 mmol —SH) of Tris(3-mercaptopropyl)trimethylolpropane (24). Subsequently 0.544 g (5.18 mol —NH$_2$) of diethanolamine was added to the thiol/SiO$_2$ mixture and mixed thoroughly ("thiol component"). 0.140 g of SiO$_2$ was homogenously dispersed in 5.182 g (17.27 mmol —C=C—) of polypopyleneoxide α-ω-bis(acrylamide) (46) ("acrylamide component"). The "thiol component" and the "acrylamide component" are combined and mixed continuously until homogeneous.

Characteristics of Resulting Biomaterial

Weight % SiO$_2$: 2.58; Gelation time: in about 30 minutes at 37° C. At 70° C. the composition is stable for 60 days; Young's modulus E at 0.1 strain is around 2 MPa. Water-uptake: 17%.

Example 36

Comparative Testing of Prior Art Biomaterials

Comparative studies were done using the materials described herein and the materials described in U.S. Pat. No. 5,874,500 to Rhee et al. ("Rhee") and WO 00/44808 to Elbert et al. ("Elber").

The material described herein had the following composition:

| Precursor Component 1: | 1,3,5,7 tetra(2-mercaptoethyl)-1,3,5,7 tetramethylcyclotetrasiloxane: | 33.0 weight % |
|---|---|---|
| Precursor Component 2: | Trimethylolpropane triacrylate | 27.7 weight % |
| Reaction Starter: | Tributylamine | 4.9 weight % |
| Syringe 1: | Precursor Component 1 | |
| Syringe 2: | Precursor Component 2 | |

The mixing was performed by connecting syringes 1 and 2 using a luer lock connector followed by transferring the content of syringe 1 and 2 from one syringe to the other approximately 5 times in order to sufficiently mix the components. The reaction initiator is added to the mixture by detaching syringes 1 and 2 and attaching a third syringe containing the initiator. The mixture is mixed using syringe to syringe mixing 25 times.

The mixture was injected into a Teflon mold to produce 12 mm high, 6 mm diameter cylindrical samples. The time of injection is defined as time zero. After 1 h, the samples are removed from the mold. At least 6 samples were prepared and stored at room conditions for 24 h. The samples were placed in polypropylene tubes with phosphate buffered saline (PBS). All tubes were placed in a water bath at 37° C. and measurements were taken after 7 days The samples were tested at a constant descending speed of the plate of 0.015 mm/s. The size of the samples was measured according to international standard ISO 5833:1992, which specifies cylinders of height 12 mm±0.1 mm and diameter 6 mm±0.1 mm. A "Zwick Materialprüfung 1456" testing machine was used.

Rhee's hydrogels are formed from polymeric networks that contain tetra-amino PEG (10,000 MW) and tetra-SE-PEG (10,000 MW) (see Rhee, Example 3). Rhee tested and provided data for the compression force (N) versus displacement (mm) for this hydrogel using an Instron Universal Tester, Model 4202 at a compression rate of 2 mm per minute using 5-mm thick disks with a diameter of 5 mm. This data is plotted in FIG. 1 of Rhee. The data in FIG. 1 of Rhee is transferred to a stress-strain curve by dividing the force measurements by the surface area of the disk ($SA=\pi r^2=\pi(2.5$ mm)$^2$) to obtain the corresponding stress value (MPa), and by dividing the displacement measurements by the original height of the disk (5 mm) to obtain the corresponding strain value.

Figure 4:
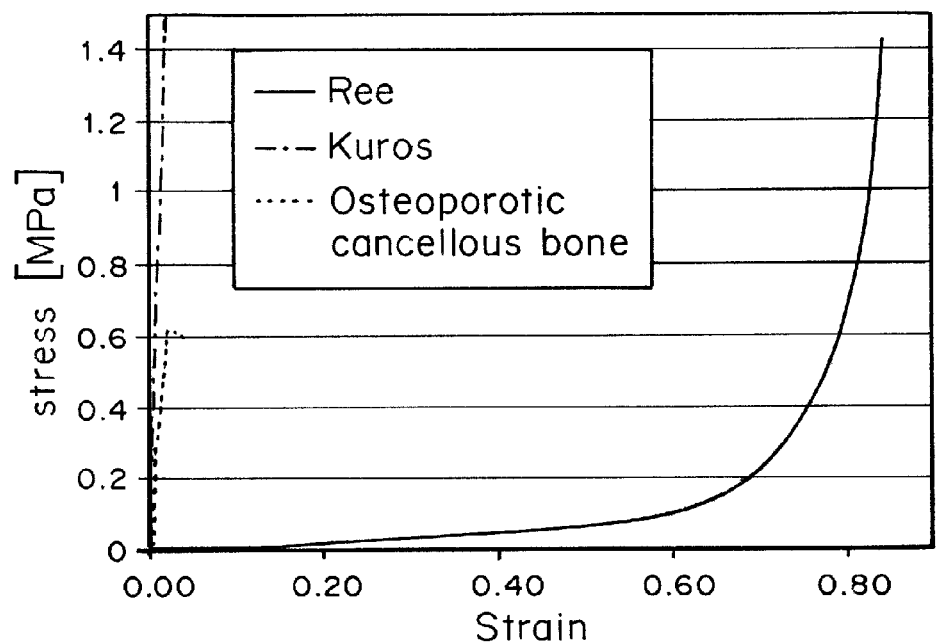
FIG. 4 is a graph comparing stress (MPa) versus strain for a prior art polymeric network forming a hydrogel and a biomaterial described herein and standard values for osteoporotic cancellous bone.

A graph of stress versus strain for the Rhee polymeric network forming the hydrogel and the claimed biomaterial and standard values for osteoporotic cancellous bone is shown in FIG. 4.

As shown in FIG. 4, the claimed biomaterial has mechanical characteristics similar to those of cancellous bone, i.e. it behaves as a linear material with a slope that is similar to the slope of cancellous bone when subjected to the same conditions. In contrast, the Rhee hydrogel does not have these properties, i.e. it behaves as a non-linear material and deforms at physiologically relevant strain and thus is not suitable to stabilize osteoporotic bone.

The results obtained with the Rhee hydrogel in FIG. 4 were independently confirmed by testing a variety of hydrogels made from precursor components of which at least one is a functionalized polyethyleneglycol. Young's modulus E for these materials was measured after swelling.

Four (4) different polymeric networks prepared from precursor components disclosed in Rhee and Elbert were produced using the concentrations listed in Table 5.

TABLE 5

Precursor components

| Biomaterial No. | Precursor 1 | Precursor 2 | Concentration (wt/wt) |
|---|---|---|---|
| 1 | 2-armed-PEG - SH (3.4 kDa) | 4-armed-PEG-acrylate (15 kDa) | 10% acrylate |
| 2 | 2-armed-PEG - SH (3.4 kDa) | 4-armed-PEG-acrylate (15 kDa) | 20% acrylate |
| 3 | 4-armed-PEG - SH (10 kDa) | 4-armed-PEG-vinyl sulfone (10 kDa) | 20% vinyl sulfone |
| 4 | 4-armed-PEG - SH (10 kDa) | 4-armed-PEG-vinyl sulfone (5 kDa) | 20% vinyl sulfone |

Synthesis: Samples were prepared by mixing the solutions of precursor 1 and 2 listed in Table 2 in TRIS buffer 0.1 M at a pH between 7.0 and 7.6. The hydrogels were formed in a 100 μl volume by pouring the mixture of precursor components into an appropriate mold. The molds containing the precursor mixture were left in an oven at 37° C. for 30 minutes. Afterwards, the samples were subjected to swelling in about 5 ml of phosphate buffered saline (PBS). The samples were kept at 37° C. for 24 hrs in the buffer solution. The percent mass increase (as a measure for swelling) was calculated by the ratio of the weight of the specimen before and after swelling (at 24 h in PBS)×100.

Testing method: Each sample was tested according to the following procedure: the diameter of each sample was measured just before placing it on the testing machine (Zwick Materialprüfung 1456). The height of the samples was measured automatically by the machine. The samples were subjected to a constant descending speed of the plate of 0.08 mm/s. E-modulus was calculated as the slope of the tangent of the stress strain curve at 10% of strain. Swelling procedure: The hydrogel samples were placed in phosphate buffered saline (PBS) solution for 1 day to establish the "swollen state" for each specimen. The increase in water uptake as a measure of the amount of swelling was measured for each of these four hydrogels.

Figure 5:
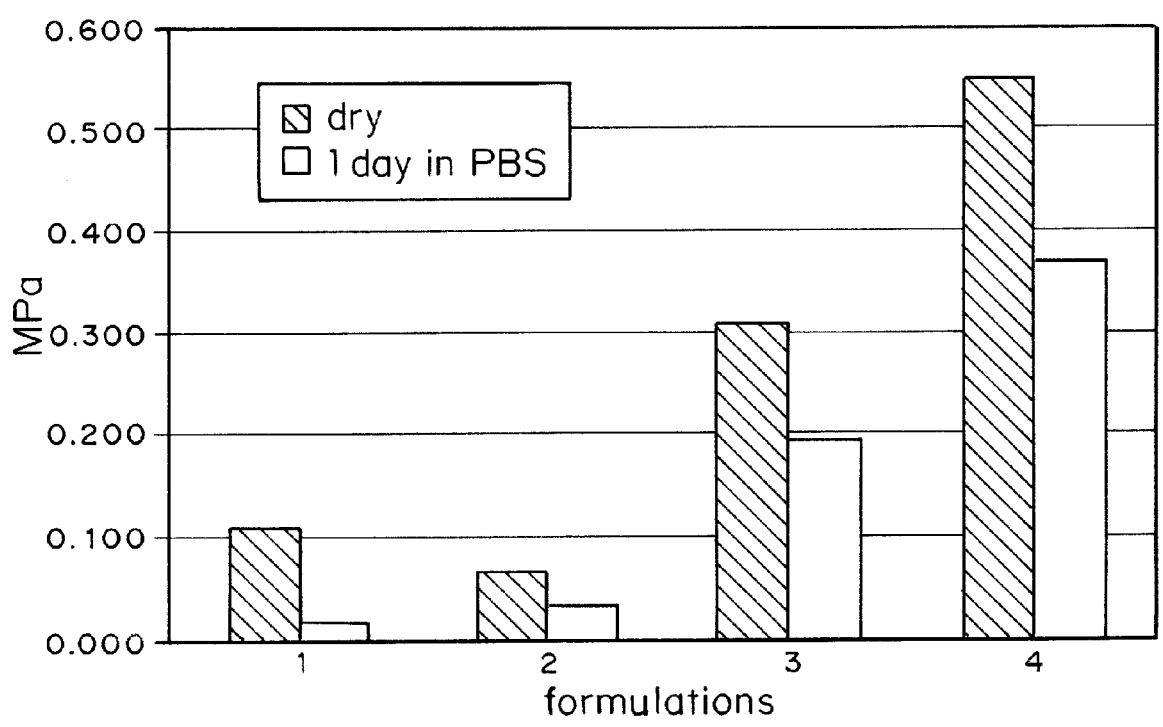
FIG. 5 is a graph comparing the Young's Modulus E (MPa) of various biomaterials in the dry state and after exposure to aqueous media.

The resulting average value for the Young's Modulus E for the four (4) hydrogels listed in Table 6 are provided in FIG. 5 before and after swelling.

As shown in FIG. 5, all of the polymeric networks forming the hydrogels tested had Young's Modulus E values of less than 0.6 MPa, both before (light-colored bars) and after (dark-colored bars) swelling. Further the Young's modulus E for each hydrogel decreased with swelling, i.e. with increased water content.

The percent mass increase (i.e., swelling) was also measured for each of the four hydrogels: hydrogel 1 increased its mass, i.e., swelled, 308%±5%; hydrogel 2 increased its mass, i.e., swelled 473%±9%; hydrogel 3 increased its mass, i.e., swelled 318%±4%; and hydrogel 4 increased its mass, i.e., swelled 290%±5%. For each of the tested materials, the mass increase (swellability) was greater than 100% after 1 day in PBS.

The Young's modulus E value for a biomaterial for hard tissue augmentation, which falls within the scope of the pending claims, was compared with the Young's modulus E values for nine (9) hydrogels prepared from precursor components according to Rhee and Elbert. The compositions of the nine hydrogels are listed in Table 6. The hydrogels were tested after swelling to determine the Young's Modulus E values.

The diameter of each sample was measured just before placing it on the testing machine and the value was entered in the machine for the evaluation of the results. The height of the samples was measured automatically by the machine. The samples were tested at a constant descending speed of the plate of 0.08 mm/s. A "Zwick materialprüfung 1456" testing machine was used. The E-modulus values were calculated as the slope of the tangent of the stress strain curve at 10% strain. The hydrogel samples were placed in phosphate buffered saline (PBS) solution for 1 day in order to swell the hydrogels.

The resulting average Young's Modulus E values for the nine (9) hydrogels listed in the last column in Table 6.

The data in Table 6 demonstrates that hydrogels made of polymer precursor components, in particular PEG polymers, even if only one of the precursors is a PEG polymer, have a Young modulus of less than 0.6 MPa when allowed to swell, i.e. simulating in vivo conditions. This is also the case when one of the precursor components is a polymer and the other is a small molecule (see materials 8 and 9).

TABLE 6

Mechanical properties of biomaterials

| Biomaterial No. | Precursor 1 | Precursor 2 | Concentration (wt/wt after formation) | Young's Modulus (MPa) of swollen specimen |
|---|---|---|---|---|
| 1 | 2-armed-PEG -SH (3.4 kDa) | 4-armed-PEG-acrylate (15 kDa) | 20% acrylate | 0.02 ± 0.002 |
| 2 | 2-armed-PEG -SH (3.4 kDa) | 4-armed-PEG-acrylate (15 kDa) | 10% acrylate | 0.01 ± 0.0008 |
| 3 | 4-armed-PEG -SH (10 kDa) | 4-armed-PEG-vinyl sulfone (10 kDa) | 20% vinyl sulfone | 0.02 ± 0.01 |
| 4 | 4-armed-PEG -SH (10 kDa) | 4-armed-PEG-vinyl sulfone (5 kDa) | 20% vinyl sulfone | 0.39 ± 0.01 |
| 5 | 4-armed-PEG -SH (5 kDa) | 8-armed-PEG-acrylate (20 kDa) | 20% acrylate | 0.28 ± 0.005 |
| 6 | 4-armed-PEG -SH (10 kDa) | 8-armed-PEG-acrylate (20 kDa) | 20% acrylate | 0.24 ± 0.016 |
| 7 | 8-armed-PEG-acrylate (20 kDa) | 4-armed-PEG -SH (3.4 kDa) | 20% acrylate | 0.13 ± 0.003 |
| 8 | 4-armed-PEG - vinyl sulfone (5 kDa) | dithiothreitol (DTT) | 20% vinyl sulfone | 0.08 ± 0.002 |
| 9 | 4-armed-PEG - vinyl sulfone (10 kDa) | dithiothreitol (DTT) | 20% vinyl sulfone | 0.05 ± 0.001 |

As shown by the data in FIG. 5 and Table 6, hydrogels formed from polymeric networks made from at least one polymer, in particular a PEG polymer, as disclosed in Rhee and Elbert, have a Young's modulus E that is less than 0.6 MPa due to the loose network and high water content. Further, Rhee discloses that the materials should swell to at least 3 times their state after formation of the hydrogels. Materials with such high degrees of swelling behave as non-linear materials and have low Young's modulus E values. Therefore, the hydrogels disclosed by Rhee and Elbert are not suitable materials for use in hard tissue augmentation.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for augmenting hard tissue, comprising applying to the tissue a composition comprising at least a first and a second precursor component,
    wherein the first precursor component comprises at least m nucleophilic groups and the second precursor component comprises at least n electrophilic groups,
    wherein m+n is at least five,
    the first and second precursor components crosslink under physiological conditions to form a biomaterial, and
    wherein uptake of water by the biomaterial does not exceed 7 weight % of the weight of the biomaterial when immersed in phosphate buffered saline at 37° C. for 24±2 hours after its formation.

2. The method of claim 1 wherein the hard tissue is at least one vertebra.

3. The method of claim 1 wherein the first and second precursor components are selected from the group consisting of monomers, oligomers, polymers, and combinations thereof.

4. The method of claim 3, wherein the first and the second precursor components are monomers.

5. The method of claim 1 wherein the first precursor component and the second precursor component form the covalent linkages by a Michael addition reaction.

6. The method of claim 1 wherein the nucleophilic groups of the first precursor component are selected from the group consisting of thiols and amines.

7. The method of claim 6 wherein the first precursor component comprises a cyclosiloxane.

8. The method of claim 7, wherein the cyclosiloxane has at least one thiol as a nucleophilic group.

9. The method of claim 6, wherein the first precursor component comprises pentaerythritol tetrakis-(3-mercaptopropyl)ether.

10. The method of claim 1 wherein the electrophilic groups of the second precursor comprise conjugated unsaturated groups.

11. The method of claim 10 wherein the conjugate unsaturated group comprises at least one acrylate group.

12. The method of claim 1 wherein the second precursor component comprises a core selected from the group consisting of 1,1,1-tris-(hydroxymethyl)propane, pentaerythritol, bis-pentaerythritol and triglycerol.

13. The method of claim 12 wherein the second precursor component comprises dipentaerythritol penta-acrylate.

14. The method of claim 1, wherein the composition further comprises one or more additives selected from the group consisting of thixotropic agents and radiopaque agents.

15. The method of claim 14, wherein the additive is barium sulfate.

16. The method of claim 1, wherein the composition further comprises a base.

17. A biomaterial for augmenting hard tissue comprising a polymeric network formed from a composition comprising at least a first and a second precursor component, wherein the first component comprises at least m nucleophilic groups and the second component comprises at least n conjugated unsaturated groups,
    wherein m+n is at least five, and
    wherein uptake of water by the biomaterial does not exceed 7 weight % of the weight of the biomaterial when immersed in phosphate buffered saline at 37° C. for 24±2 hours after its formation.

18. The biomaterial of claim 17 wherein the second precursor component comprises a core selected from the group consisting of 1,1,1-tris-(hydroxymethyl)propane, pentaerythritol, bis-pentaerythritol and triglycerol.

19. The biomaterial of claim 17 wherein the second precursor component comprises dipentaerythritol penta-acrylate.

20. The biomaterial of claim 17, wherein the composition further comprises one or more additives selected from the group consisting of thixotropic agents and radiopaque agents.

21. The biomaterial of claim 20, wherein the additive is barium sulfate.

22. The biomaterial of claim 17, wherein the first component comprises a cyclosiloxane having at least one thiol as a nucleophilic group, and wherein the conjugated unsaturated groups comprise at least one acrylate.

23. The biomaterial of claim 17, wherein the first precursor comprises pentaerythritol tetrakis-(3-mercaptopropyl)ether.

24. A kit for forming in situ crosslinkable composition for augmenting a hard tissue comprising at least a first precursor component and a second precursor component,
    wherein the first and the second precursor components are monomers, oligomers or polymers,
    wherein the first precursor component comprises at least m nucleophilic groups and the second precursor component comprises at least n electrophilic groups,
    wherein m+n is at least five,
    the first and second precursor components crosslink under physiological conditions to form a biomaterial, and
    wherein uptake of water by the biomaterial does not exceed 7 weight % of the weight of the biomaterial when immersed in phosphate buffered saline at 37° C. for 24±2 hours after its formation.

25. The kit of claim 24 wherein the first precursor component comprises a cyclosiloxane.

26. The kit of claim 24 wherein the second precursor component comprises a core selected from the group consisting of 1,1,1-tris-(hydroxymethyl)propane, pentaerythritol, bis-pentaerythritol and triglycerol.

27. The kit of claim 26 wherein the second precursor component comprises dipentaerythritol penta-acrylate.

28. The kit of claim 24, further comprising one or more additives selected from the group consisting of thixotropic agents and radiopaque agents.

29. The kit of claim 28, wherein the additive is barium sulfate.

30. The kit of claim 24, wherein the first precursor is pentaerythritol-tetrakis-(3-mercaptopropyl)ether.

* * * * *